United States Patent
Van Damme et al.

(10) Patent No.: US 9,931,472 B2
(45) Date of Patent: Apr. 3, 2018

(54) INTRADERMAL INJECTION DEVICE

(71) Applicants: UNIVERSITEIT ANTWERPEN, Antwerp (BE); VOXDALE BVBA, Antwerp (BE)

(72) Inventors: Pierre Van Damme, Kontich (BE); Vanessa Vankerckhoven, Wilrijk (BE); Stijn Verwulgen, Schoten (BE); Ruben Camerlynck, Ieper (BE); Wouter Coemans, Neerpelt (BE); Linda Scheelen, Mol (BE); Koen Catharina Lodewijk Beyers, Wuustwezel (BE); Bart Verleije, Kalmthout (BE); Wim Boudewijns, Brasschaat (BE)

(73) Assignees: UNIVERSITEIT ANTWERPEN, Antwerp (BE); VOXDALE BVBA, Antwerp (BE); NOVOSANIS NV, Wijnegem (BE)

( * ) Notice: Subject to any disclaimer, the term of this patent is extended or adjusted under 35 U.S.C. 154(b) by 737 days.

(21) Appl. No.: 14/395,133

(22) PCT Filed: Apr. 17, 2013

(86) PCT No.: PCT/EP2013/057990
§ 371 (c)(1),
(2) Date: Oct. 17, 2014

(87) PCT Pub. No.: WO2013/156524
PCT Pub. Date: Oct. 24, 2013

(65) Prior Publication Data
US 2015/0073344 A1  Mar. 12, 2015

(30) Foreign Application Priority Data
Apr. 17, 2012 (GB) .................... 1206766.6

(51) Int. Cl.
*A61M 5/00* (2006.01)
*A61M 5/315* (2006.01)
(Continued)

(52) U.S. Cl.
CPC ...... *A61M 5/31501* (2013.01); *A61M 5/2425* (2013.01); *A61M 5/326* (2013.01);
(Continued)

(58) Field of Classification Search
CPC ........... A61M 2005/31508; A61M 2005/3151; A61M 5/2425; A61M 5/2466;
(Continued)

(56) References Cited

U.S. PATENT DOCUMENTS 3,066,670 A    12/1962  Stauffer
4,227,528 A    10/1980  Wardlaw
(Continued)

FOREIGN PATENT DOCUMENTS

CN    1604799 A     4/2005
CN    101068586 A   11/2007
(Continued)

OTHER PUBLICATIONS

Chinese Office Action for Chinese Application No. 201380031848. 4, dated Jul. 19, 2016.
(Continued)

*Primary Examiner* — Jason Flick
(74) *Attorney, Agent, or Firm* — Workman Nydegger

(57) ABSTRACT

An intradermal injection device comprises a housing, a foot with an opening for passage of a needle; a reservoir movably mounted in the housing, and having a hollow space for holding a fluid; a hollow needle movably mounted in the housing and having a first end for penetrating the subject's skin and a second end for penetrating the reservoir, a plunger movably mounted in the housing for moving the needle
(Continued)

through the opening for penetrating the subject's skin, and for pressing the fluid out of the reservoir. The reservoir is frictionally mounted inside the housing by first friction means, and the plunger is frictionally mounted to the reservoir by second friction means. The force to overcome the second friction is larger than the force to overcome the first friction.

13 Claims, 23 Drawing Sheets

(51) Int. Cl.
- *A61M 5/24* (2006.01)
- *A61M 5/32* (2006.01)
- *A61M 5/34* (2006.01)
- *A61M 5/42* (2006.01)
- *A61M 5/46* (2006.01)

(52) U.S. Cl.
CPC ......... *A61M 5/3232* (2013.01); *A61M 5/2466* (2013.01); *A61M 5/3271* (2013.01); *A61M 5/3272* (2013.01); *A61M 5/3293* (2013.01); *A61M 5/345* (2013.01); *A61M 5/425* (2013.01); *A61M 5/46* (2013.01); *A61M 2005/3151* (2013.01); *A61M 2005/31508* (2013.01)

(58) Field of Classification Search
CPC ............ A61M 5/31501; A61M 5/3232; A61M 5/326; A61M 5/3271; A61M 5/3272; A61M 5/3293; A61M 5/345; A61M 5/425; A61M 5/46
USPC ........................................................ 604/110
See application file for complete search history.

(56) References Cited

U.S. PATENT DOCUMENTS

| | | | |
|---|---|---|---|
| 5,358,491 A | | 10/1994 | Johnson et al. |
| 5,616,128 A | * | 4/1997 | Meyer ................. A61M 5/2033 604/139 |
| 7,569,035 B1 | | 8/2009 | Wilmot et al. |
| 8,444,606 B2 | | 5/2013 | Radmer et al. |
| 8,597,257 B2 | | 12/2013 | Modi |
| 8,632,508 B2 | | 1/2014 | Hansen et al. |
| 9,242,044 B2 | | 1/2016 | Markussen |
| 2006/0229570 A1 | | 10/2006 | Lovell et al. |
| 2007/0191780 A1 | | 8/2007 | Modi |
| 2008/0287883 A1 | | 11/2008 | Radmer et al. |
| 2008/0312591 A1 | | 12/2008 | Harrison |
| 2009/0192486 A1 | | 7/2009 | Wilmot et al. |
| 2010/0179485 A1 | | 7/2010 | Radmer et al. |
| 2010/0241066 A1 | | 9/2010 | Hansen et al. |
| 2010/0280460 A1 | | 11/2010 | Markussen |
| 2011/0319834 A1 | | 12/2011 | Modi |
| 2013/0150799 A1 | | 6/2013 | Radmer et al. |
| 2013/0211330 A1 | * | 8/2013 | Pedersen ............. A61M 5/2033 604/111 |
| 2014/0207078 A1 | | 7/2014 | Modi |
| 2015/0273152 A1 | | 10/2015 | Modi et al. |

FOREIGN PATENT DOCUMENTS

| | | |
|---|---|---|
| CN | 101454034 A | 6/2009 |
| EP | 2554207 A1 | 2/2013 |
| GB | 2482241 A | 1/2012 |
| JP | H07148258 A | 6/1995 |
| JP | H07505563 A | 6/1995 |
| JP | H11500938 A | 1/1999 |
| JP | 2008500853 A | 1/2008 |
| JP | 2009125312 A | 6/2009 |
| JP | 2009526575 A | 7/2009 |
| JP | 2010532243 A | 10/2010 |
| WO | 2003068290 A2 | 8/2003 |
| WO | 2007002052 A2 | 1/2007 |
| WO | 2007093051 A1 | 8/2007 |
| WO | 2011122395 A1 | 10/2011 |
| WO | 2012022810 A2 | 2/2012 |

OTHER PUBLICATIONS

Japanese Office Action from JP Application No. 2015-506227, dated Feb. 7, 2017.
Netherlands Search Report for Corresponding Netherlands Application No. 2010649, dated Feb. 10, 2015.
Great Britain Search Report for corresponding Great Britain Application No. 1206766.6, dated Aug. 16, 2012.
International Search Report for corresponding International PCT Application No. PCT/EP2013/057990, dated Jun. 26, 2013.
Japanese Office Action from JP Application No. 2015-506227, dated Dec. 12, 2017.

* cited by examiner

FIG.33
FIG.34
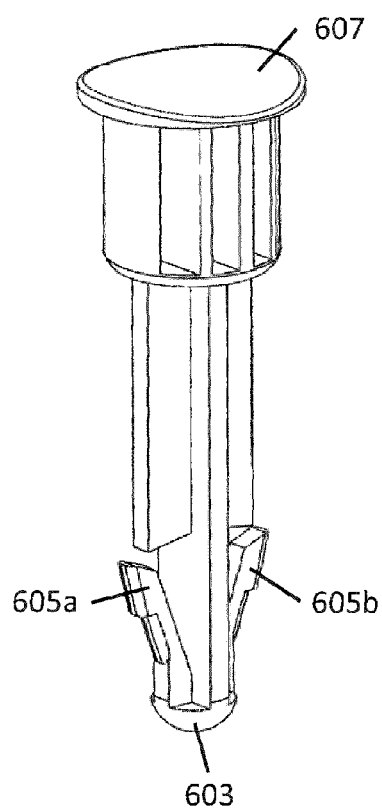
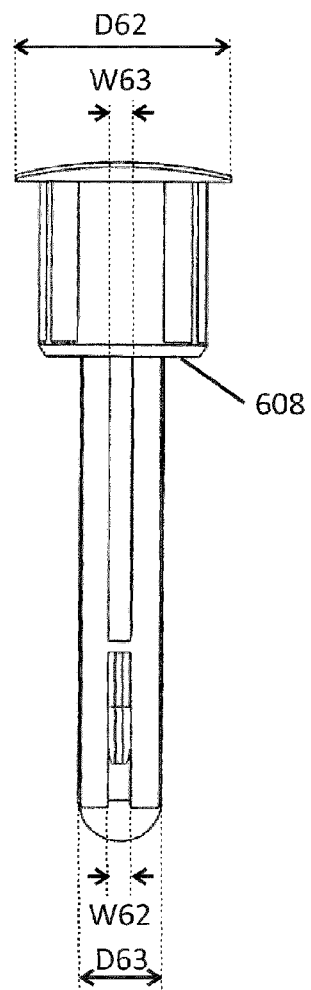

INTRADERMAL INJECTION DEVICE

FIELD OF THE INVENTION

The present invention relates to the field of intradermal injection devices, more specifically to the field of prefillable or prefilled injection devices. The present invention relates to the devices per se, methods of manufacturing and methods of operation thereof.

BACKGROUND OF THE INVENTION

The vast majority of vaccines are administered into the muscle (intramusculary, IM) or into subcutaneous fat (subcutaneously, SC) using needle and syringe. Mammalian skin is composed of two primary layers: the epidermis and the dermis. The epidermis is the outer layer of the skin and it has a thickness of 150-200 µm, while the dermis which is the inner layer has a thickness of 1.5-3.0 mm. The skin thickness varies with age, gender and anatomic site, but also racial and regional differences have been reported. Underlying the dermis is the hypodermis which is not part of the skin, but connects the skin to bone and muscle.

The standard procedure for intradermal injection of substances, i.e. injection in the dermis of the skin, is the Mantoux technique. This requires the vaccinator to judge the angle and depth of needle insertion by eye/feel, which requires special training for medical staff and may not reliably target skin as it can result in technical errors and variability of dose delivery. The Mantoux technique is nonetheless used as the route of choice for a very limited number of vaccines, such as *Bacillus* Calmette-Guérin for tuberculosis, and in some developing countries for rabies vaccination.

The unique immunological properties of the skin make the epidermis and dermis attractive sites for prophylactic and therapeutic vaccination. Skin dendritic cells are important professional antigen-presenting cells that have potent T-cell activating properties upon pathogenic challenge. These favourable immunological properties of the skin allow the use of reduced doses, which makes intradermal delivery of substances an attractive alternative to IM/SC delivery.

The World Health Organization has estimated that annually about 8-16 million Hepatitis B infections, 2-5 million Hepatitis C infections and 80,000-160,000 HIV infections occur because of needle stick accidents and the re-use of disposables needles and syringes. Safe ID devices that prevent needle stick accidents as well as re-use of the injecting material could provide an answer and have become a high priority for global health.

SUMMARY OF THE INVENTION

It is an object of embodiments of the present invention to provide an injection device (syringe) which can be used to administer vaccines (or drugs) by the intra-dermal (ID) route.

According to inventive aspects of the invention, the device allows reduction of spilling and/or waste of liquid, and/or liquid left behind in the syringe.

According to the same or further inventive aspects of the invention, the device allows to reduce the required amount of antigen dose capacity.

According to the same or further inventive aspects of the invention, the device offers an increased ease of use, in particular such that the correct penetration depth of the needle is guaranteed, even when administered by non-medical staff.

According to the same or further inventive aspects of the invention, the device allows a cost reduction as compared to the currently available IM devices, in particular in terms of ease of assembly, reduced amount of materials and reduced amount of liquid.

According to the same or further inventive aspects of the invention, the device offers a similar or better immune response than with IM (intra-muscular) administration.

According to the same or further inventive aspects of the invention, the device offers increased safety, e.g. to prevent accidental needle sticks.

In one aspect, the present invention provides an intradermal injection device, comprising: a housing; a foot mounted to the housing and having a surface which can be placed on a subject's skin to be injected, the foot having an opening for allowing passage of a needle; a reservoir movably mounted in the housing, and having a hollow space for holding a fluid to be administered to the subject; a hollow needle movably mounted in the housing such that it can selectively protrude through the opening or be retracted from the opening, and having a first end for penetrating the subject's skin and a second end for penetrating the reservoir, the first end having a first opening for administering the fluid to the subject, the second end having a second opening for accepting the fluid from the reservoir and passing it through the needle to the first end; a plunger movably mounted in the housing for moving the needle through the opening for penetrating the subject's skin, and for pressing the fluid out of the reservoir into the needle; wherein the reservoir is frictionally mounted inside the housing by first friction means, and the plunger is frictionally mounted to the reservoir by second friction means in such a way that the force required to overcome the resistance to move the plunger with respect to the reservoir (i.e. to overcome the second friction) is at least a predetermined amount larger than the force required to overcome the friction to move the reservoir with respect to the housing (i.e. to overcome the first friction), the predetermined amount being a value of at least 0.5 Newton.

It is an advantage of providing a foot having a surface which can be placed on a subject's skin, because this allows to accurately determine the penetration depth of the needle inside the skin, which is important for the efficiency of intradermal injections.

Although it is known in the art that the dose required for achieving a therapeutic and/or prophylactic effect (at least for some vaccines) can be reduced by using intradermal injections as opposed to other types of injections, such as e.g. intramuscular, in practice a certain amount of overfill is used, because not all of the fluid will actually be injected in the subject's skin.

It is an advantage of the present invention that the plunger is frictionally mounted to the reservoir, whereby the force required to move the plunger relative to the reservoir is at least a predefined amount larger than the force required to move the reservoir with respect to the housing. This has the effect that, when a force is applied to the plunger, the plunger and the reservoir and the needle will move together towards the opening, while maintaining their relative position. This initial movement will cause the needle to penetrate the subject's skin, while minimal or substantially no pressure is exerted on the fluid in the reservoir (because the position between the plunger and the reservoir is maintained), hence no or only a limited amount of fluid will leave the needle before being inserted in the skin. The plunger and reservoir and needle will typically move towards the opening until a predefined end position is reached, corresponding to a predefined depth of the needle into the subject's skin, at which point they come to a stop. When a force higher than the force required to overcome the friction between the plunger and the reservoir is then exerted upon the plunger, the reservoir and the needle will maintain their position, but the plunger will move relative to the reservoir, and will thereby squeeze the fluid out of the reservoir, through the needle, and into the subject's skin. Thus the friction between the plunger and the reservoir makes sure that the needle is first inserted into the subject's skin, before pressure is exerted upon the fluid in the reservoir, so that spilling of the fluid is avoided, and the amount of overfill can be reduced.

It is noted that the same effect will happen also when a force larger than the force required to overcome the friction between the plunger and the reservoir is exerted on the plunger already from the start, hence the same effect is obtained irrespective of the force profile applied on the plunger.

It is noted that the predetermined value of at least 0.5 Newton is chosen on the one hand as larger than the force required to insert the envisioned needles into a typical human subject's skin, and to provide sufficient headroom for production tolerances, and on the other hand is chosen sufficiently small so that the force required to be applied on the plunger surface for performing the intradermal injection is not excessive, meaning that it can be relatively easily performed by a pointing finger. In preferred embodiments of the invention, the predetermined value is chosen in the range of 0.5 to 30.0 Newton. This value can e.g. be chosen differently depending on the type of needle, or for different skin locations envisioned to be injected, or for different target groups of subjects to be injected.

It is an advantage that for a proper administration of the fluid to the subject, only a proper position of the foot of the device on the subject's skin, and a force substantially perpendicular to the subject's skin are required. This does not require highly trained staff.

By providing a syringe with a built-in reservoir, the amount of fluid (to be contained in the device, and thus the amount of fluid to be injected) can be accurately determined (based on the dimensions of the reservoir). Yet, this reservoir can be separately filled and assembled, e.g. filled with a vaccine in a first facility, and then assembled with the other parts (a.o. the needle) in another facility. This is a huge advantage over existing devices, where the needle and the actual reservoir are inter. In addition, the number of doses and the number of needles is equal, thereby preventing double usage of a single needle. In addition, the number of manual operations is reduced, thus the risk for human errors is reduced. In addition, the risk of spilling liquid is reduced. In addition, the length of tubular connections can be reduced, thus also the amount of liquid required.

Where in the present invention reference is made to "element A is frictionally mounted to element B", what is meant is that "element A is movably mounted to B", but movement will only occur when a predetermined force, e.g. to overcome a friction or a resistance between A and B, is applied.

In this document, the term "reservoir" can refer to a certain part with reference number 3, or to a hollow space 312 for containing a liquid, which is a part thereof. It will be clear from the context and/or from the reference numerals what is meant. The space 312 is sometimes also referred to as the "actual reservoir" or "hollow space" or "filled space".

In an embodiment, the reservoir comprises a cavity for receiving the second end of the needle, the cavity being in fluid connection with the hollow space and having a volume less than 3% of the volume of the hollow space, preferably less than 2%, more preferably less than 1%.

The cavity is preferably a cylindrical cavity dimensioned for protecting the second end of the needle, when the needle has penetrated the reservoir during activation of the device, against potential damage by the plunger movement. The cavity is preferably located at a bottom end of the hollow space. The cavity offers the advantage that substantially all of the liquid in the hollow space will be squeezed out of the reservoir into the needle, while only the fraction within the cavity will remain in the device after administration. In this way, the amount of overfill of liquid, e.g. vaccine, can be further reduced.

In an embodiment, the reservoir has a dividing wall forming a bottom of a hollow space for holding the fluid, and wherein the plunger has a plunger head with a shape complementary to the shape of the dividing wall.

Providing complementary shapes to the plunger head and to the bottom of the hollow space assures that most of the liquid is pushed out of the reservoir when the plunger is moved into the reservoir during administration of the fluid. This helps to further reduce the amount of overfill.

In an embodiment, the intradermal injection device further comprises an elastic seal for closing the hollow space, and for squeezing substantially all of the fluid out of the hollow space when the plunger is moved towards the needle.

The seal is preferably made of a flexible plastic material, e.g. an elastic material, such that, when the plunger is moved towards the needle when administering the fluid, the seal is sandwiched between a plunger head and the bottom of the hollow space (also called "dividing wall"), so as to completely fill the space between the plunger head and the bottom of the cavity, thereby squeezing all of the fluid out of the hollow space and into the needle (or into the cavity). Hence the flexible or elastic seal also helps to further reduce the amount of overfill of liquid, by further reducing the amount of liquid left in the hollow space.

The seal also has the function of closing the hollow space so that the fluid, e.g. vaccine, can be introduced into the reservoir before the plunger is mounted thereto, or in other words, before the injection device is completely assembled. This allows a separate filling stage of the fluid, and a separate further assembly stage of the device, which is a huge advantage over existing devices.

The dimensions of the reservoir (component) and seal define the amount of fluid in the device. In particular embodiments, the seal can only be mounted in a single position within the reservoir, for defining a single volume. When using such embodiments, a single "type" of device (defined at the design-stage) corresponds to a single amount of fluid. In other particular embodiments, the reservoir may e.g. have multiple circumferential grooves, for receiving a circumferential protrusion of the seal. In such embodiments, one out of a set of predefined volumes can be selected at the filling-stage, while using a single "type" of reservoir and seal. In yet other embodiments, a single reservoir component can be used in combination with a plurality of seals having different dimensions, for defining different volumes of the actual reservoir.

In an embodiment of the intradermal injection device, the needle is fixedly mounted in a needle hub, the needle hub being movably mounted between the foot and the reservoir, and wherein the needle has an inner diameter in the range of 0.0826 mm to 0.260 mm.

By fixedly mounting the needle in a needle hub, and by providing an opening in the foot for allowing protrusion of part of the needle, mechanical support is provided to the needle, which is prevented from bending, allowing the inner diameter of the needle to be selected as small as 0.260 mm (26 G), or even 0.159 mm (30 G) or even 0.0826 mm (34 G). Hence, the amount of liquid left behind in the needle, after administration of the fluid, e.g. vaccine, is minimised, thus the amount of overfill can be further reduced. The shape and dimensions of the foot and the reservoir can accurately determine the predetermined distance that the needle hub, and thus the needle can move.

In an embodiment of the intradermal injection device, the needle hub is movably mounted between the foot and the reservoir by means of a wall extending from the foot, the wall and the needle hub being adapted to engage, so as to allow axial movement with respect to the foot.

The wall may have an upright shape having an inner shape complementary to an outer shape of the needle hub, so as to mutually engage.

In an embodiment of the intradermal injection device, the needle is fixedly mounted in a needle hub, and the needle hub has at least one protruding pen adapted for being received in at least one groove of the reservoir; and the housing comprises a tubular case having a first end for receiving the plunger and a second end for receiving the reservoir and the needle hub and the foot; and the foot has means for angularly engaging the needle hub, the case having a groove ending in an opening for receiving a pen protruding from the reservoir for movably mounting the reservoir to the case, the case further having another groove for receiving at least one pen penetrating inwardly from the foot for movably mounting the foot to the case.

This mechanical arrangement allows the foot to be movably (in particular rotationally) mounted to the case, thereby enclosing the needle hub and the reservoir. Although the detailed mechanisms will be explained further, the main mechanical movements are already indicated here:

Due to the angular engagement between the foot and the needle hub, rotation of the foot will result in rotation and axial displacement of the needle hub. This will allow activation of the device.

The needle hub can axially move with respect to the reservoir for allowing the second needle end to penetrate the reservoir, and can axially move with respect to the foot for allowing the first needle end to pass through the opening for penetrating the subject's skin.

The plunger can axially move towards the reservoir for (first) moving the needle hub and the reservoir together towards the opening, and can then further move with respect to the reservoir for pushing the liquid out of the hollow space.

The device has multiple modes of operation, in particular a locked mode (after assembly), an activated mode (after rotation of the foot), and a safety mode (after the plunger has been pushed and released).

The angular engagement means may be formed by a wall section of the foot having an inner shape complementary to an outer shape of the needle hub, or vice versa.

In an embodiment of the intradermal injection device, the case has at least one opening for receiving at least one rib of a plunger for preventing rotation of the plunger, and wherein the plunger has snaps not being aligned above grooves of the reservoir in a locked mode, and the reservoir has protruding pens received in a circumferential groove of the case, so that the plunger and the reservoir are prevented from axial movement in the locked mode.

In the locked mode, which is the mode of the device right after assembly, the plunger cannot move towards the opening, because its snaps cannot penetrate the alignment grooves of the reservoir. And the reservoir cannot move in axial direction because its protruding pens are located in circumferential grooves of the case. And since the needle hub is connected to the reservoir (as described above), the needle also cannot move axially, even when the plunger is being pressed.

It is an advantage of the device having a locked mode in that the needle cannot accidentally penetrate the actual reservoir, and will not penetrate through the opening, even when a force is exerted upon the plunger, e.g. during transport. In this way the risk for loss of fluid is minimized, and the risk for needle stick accidents is also minimized.

In an embodiment of the intradermal injection device, the groove of the reservoir is inclined with respect to a plane perpendicular to the longitudinal axis of the device, and the case further comprises longitudinal grooves in connection with the opening, such that a rotation of the foot results in an axial displacement of the needle hub towards the reservoir, and such that the protruding pens are moved into the longitudinal grooves, and such that the snaps of the plunger are aligned above the grooves of the reservoir in an unlocked mode.

When the foot is rotated over a predefined angle, e.g. an angle in the range from 10° to 180°, preferably in the range of 10° to 120°, e.g. about 75°, the angular engagement means will cause the needle hub to rotate along with the foot, by which the needle hub will then be displaced axially as its protruding pens move along the inclined groove of the reservoir. This movement of the foot will cause the second needle end to penetrate a bottom part (e.g. the cavity as described above, if present) of the reservoir.

When the pen (of the needle hub) has reached an end position inside the groove (of the reservoir), further rotation of the foot will force the reservoir to rotate, by moving the pens (of the reservoir, which pens were located in the opening of the case), into the longitudinal grooves of the case. The rotation of the reservoir will also align the grooves of the reservoir underneath the snaps of the plunger. After the foot and the reservoir are rotated over a first resp. second predefined angle, the device is in unlocked mode, also called "activated" mode.

In this mode, the first end of the needle has penetrated the reservoir, but the second end of the needle is still inside the housing of the device. No pressure is exerted upon the fluid yet, thus substantially no fluid will escape from the reservoir through the needle. However, there are no obstacles anymore preventing the plunger to be moved towards the needle (only friction forces for holding it in place against gravity and/or inertial forces due to movement of the device).

At this point, the device would normally be placed on the subject's skin. As described above, when a force is subsequently applied to the plunger, the plunger and the reservoir and the needle will first move together towards the opening, while maintaining their relative position. This initial movement will cause the needle to penetrate the subject's skin. When the plunger and reservoir have reached a predefined end position, e.g. when a surface of the reservoir contacts the surface of the foot, the second end of the needle will have reached a predefined depth into the subject's skin. When a force, higher than the force required to overcome the friction between the plunger and the reservoir is exerted upon the plunger, the reservoir and the needle will maintain their position, but the plunger will move further towards the reservoir, and will thereby squeeze the fluid out of the reservoir, through the needle, and into the subject's skin.

It is an advantage that a rotational movement is required to unlock the device, because the risk that the foot is accidentally rotated with respect to the case, e.g. during transport, is negligible, especially when in addition some resistance (or other kind of friction) needs to be overcome.

In an embodiment of the intradermal injection device, the groove of the case has at least one rib forming a hook for obstructing the pen of the foot for preserving the angular position of the foot with respect to the case.

The rib acts as an obstacle for preventing the foot to be turned back, once the first end of the needle has penetrated the reservoir. This prevents that the needle is withdrawn from the reservoir, once it has penetrated into the reservoir. By preventing such withdrawal of the needle, the risk of contamination of the fluid, or of leakage of the fluid, e.g. due to inadvertent behaviour, is minimized.

In an embodiment of the intradermal injection device, the longitudinal grooves of the case comprise at least one snap for exerting a pressure directed inwardly upon the protruding pens of the reservoir for creating the frictional mounting between the case and the reservoir, and the protruding pens of the reservoir have a bevel for enabling the move of the protruding pens from the opening towards the longitudinal grooves against the pressure of the snaps.

The friction caused by the snaps prevents that the reservoir can glide in the longitudinal grooves unintentionally, e.g. under the gravity force.

The bevel prevents that the protrusions would be blocked by an edge of the snap, and hence facilitate its insertion into the longitudinal groove.

In an embodiment, the intradermal injection device furthermore comprises safety locking means comprising a spring for withdrawing the needle back into the opening when pressure on the plunger is released and the device is in unlocked mode, and for blocking the needle after being withdrawn.

The spring is arranged between the plunger and the case, such that it is compressed when the plunger is moved towards the reservoir. When the plunger is in its distal position (closest to the cavity), the energy stored in the spring is largest. When pressure on the plunger is released (which normally occurs after the fluid is administered to the subject), the spring will automatically push the plunger back (upwards), and the reservoir and the needle hub and the needle along with it.

When fully retracted, the plunger and the reservoir and the needle are blocked, and the device is in a safety locked mode. In this mode, the second end of the needle does not extend through the foot opening, so that needle stick accidents are avoided.

In an embodiment of the intradermal injection device, the plunger has at least one snap head, and the groove of the reservoir has at least one opening for receiving the snap head when the plunger has reached its distal position for permanently fixing the position of the plunger with respect to the reservoir; and the groove of the case further has an open end for receiving the pen of the reservoir when the reservoir is completely withdrawn, and wherein the snap of the case further has a top end for permanently fixing the position of the reservoir with respect to the case. This describes one embodiment of the safety locking means. In the safety locked mode, the reservoir is not movable anymore with respect to the case, and the plunger is not movable anymore with respect to the reservoir, and thus also with respect to the case. Hence, in the safety locked mode, all parts of the device are in a fixed position with respect to the case, so that needle stick accidents are avoided.

Embodiments of the intradermal injection device according to the present invention may thus be in one of three modes (after assembly):

1) a locked mode, wherein the plunger is prevented from moving axially, but the foot (and needle hub and reservoir) can be rotated, 2) an unlocked mode wherein the plunger (and needle and reservoir) are allowed to be moved axially for emptying the reservoir, and for allowing the needle to extend through the opening for penetrating the skin when a force is exerted upon the plunger, and for retracting the needle back into the opening, and further retracting the plunger and needle and reservoir, 3) a safety mode, wherein axial movement is permanently blocked, after the plunger and needle and reservoir are fully retracted by means of a spring.

When the device is being brought from the locked mode to the unlocked mode by rotation of the foot, bevels may facilitate movement of the foot with respect to the case, while at the same time providing a tactile feedback to the user, each time the pens pass the at least one bevel. The edge gives feedback that the end position is reached, and that the device is activated (i.e. in unlocked mode). The hook holds the rotated foot in position, and prevents it from being rotated back.

When intra-dermal injections are applied correctly, the subject suffers less pain after the injection. Correct application of the injection is achieved by the syringe according to embodiments of the present invention, having the features mentioned.

When in the locked mode, the needle is withdrawn (retracted) in the opening of the foot. This offers the advantage that the immunity of the needle is maximally guaranteed, and the risk of accidentally touching the needle (thus causing infections or bleeding), and breaking or bending the needle tip is eliminated.

In the locked mode, the plunger is being prevented from being pressed towards the reservoir. This offers the advantage that the risk of accidental misuse is reduced to a minimum.

By providing a foot with a surface that can be placed on the skin of the subject and be pressed thereto by a force of e.g. 0.5 to 10 Newton, while still being clamped between e.g. thumb and middle finger or ring finger, the syringe according to embodiments of the present invention can be easily positioned substantially perpendicular to the skin, and the liquid can be injected gently. By further providing a plunger and needle that can longitudinally move over a predefined distance with respect to the foot, the penetration depth of the needle can be accurately determined, and the risk of leakage can be highly reduced, if not eliminated.

Because the depth of the needle into the skin is determined by the device, the need for training medical personnel can be highly reduced. Instead of learning to correctly apply ID injections, which may take weeks or months of training, they only need to be trained how to correctly use the device, which can be learned in less than an hour, even for not highly educated people.

Thanks to the safety locking means, the needle is automatically drawn back into the device, and prevented from moving again. This mechanism may be even more important for reducing the risk of spreading diseases by accidental puncture or by reusing a same needle for multiple subjects.

Yet another advantage of the device is that ID injection requires less fluid than with intramuscular (IM) injections for obtaining a same therapeutic and/or prophylactic and/or immunological effect.

An advantage of building-in the needle into the syringe, is that the syringe can provide mechanical support to the needle. This allows the needle diameter to be reduced without increasing the risk of bending the needle, and this in turn allows the amount of fluid in the reservoir to be reduced. This not only reduces the cost of the device, but also increases the effective number of doses that can be obtained from a certain amount of vaccine (read: number of subjects that can be treated).

BRIEF DESCRIPTION OF THE DRAWINGS

FIG. 33 shows a perspective view of the plunger of FIG. 32 from above.

FIG. 34 shows a side view of the plunger of FIG. 32.

Figure 1:
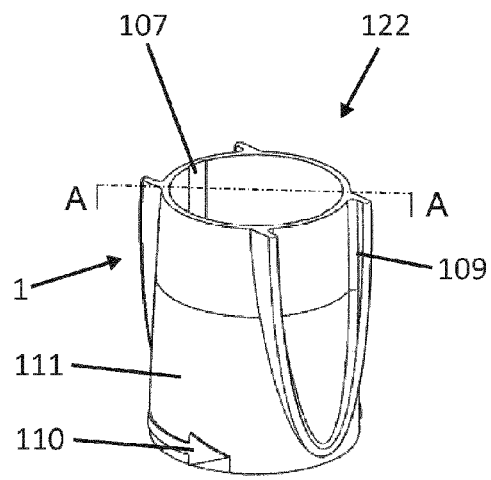
FIG. 1 shows a perspective view of an embodiment of the foot (first part) of a syringe according to embodiments of the present invention, shown from above.

The drawings are only schematic and are not limiting. In the different drawings, the same reference signs refer to the same of analogous elements.

DETAILED DESCRIPTION OF THE INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

In this document, the terms "unlocked mode" and "activated mode" have the same meaning.

In this document, sometimes the word "down" is used to indicate a direction from the plunger surface 607 towards the opening 102, and the word "up" is used to indicate the opposite direction, for ease of explanation.

Figure 40:
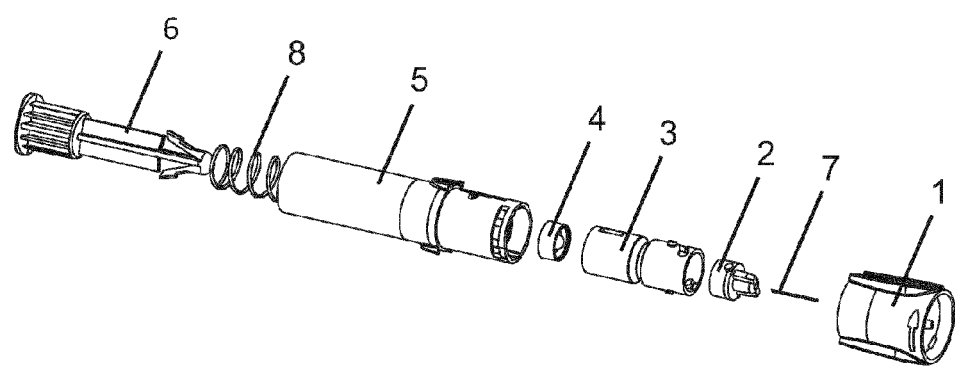
FIG. 40 shows an exploded view of the parts 1-8 of the device.

The invention comprises eight parts placed in relation to each other, and which may be placed in relation to the operator and the subject's skin. The eight parts are shown in an exploded view in FIG. 40, further referred to as respectively the foot 1 (the first part), the needle hub 2 (the second part), the reservoir 3 (the third part), the seal 4 (the fourth part), the case 5 (the fifth part), the plunger 6 (the sixth part), the needle 7 (the seventh part) and the spring 8 (the eighth part).

The Foot, Also Referred to as the First Part

The first part, the foot 1, will be explained with reference to FIGS. 1-4. As shown in FIG. 1, the foot 1 has a hollow tubular shape, e.g. a substantially cylindrical or conical tubular shape, delimited by a wall 111. The foot 1 is closed at its bottom end 121 and open at its top end 122. On the outside of the foot 1, indications 110 may be provided, for example an arrow, a colour code, a text or another sign, for example to indicate the direction in which the foot 1 needs to be rotated for activation of the device 9. On the outside of the wall 111, protrusions 109 may be provided to provide support for finger placement. These protrusions 109 may be designed so that they align with the protrusions 517a, 517b on the case 5 (fifth part) when the activation of the device 9 is complete.

Relation to the Skin

Figure 3:
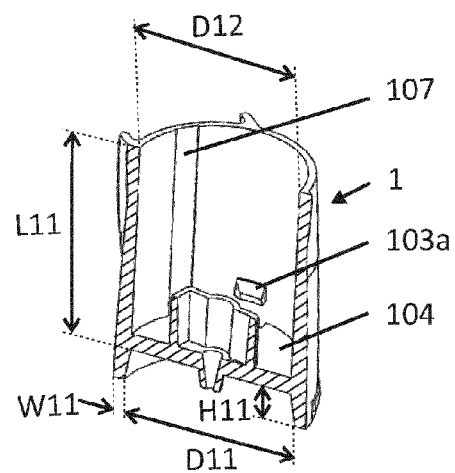
FIG. 3 shows the rear fraction of the foot of FIG. 1 when cut by plane A-A.

The bottom end 121 has a collar 101 allowing the foot 1 (and thus the entire device 9) to be placed substantially perpendicularly onto the subject's skin 91, and has dimensions D11, H11 (D11 being the diameter of the collar 101, and H11 being the height of the collar 101, as illustrated in FIG. 3) for allowing the skin to slightly bend upwards towards an opening 102 in a closing face 104 closing the foot 1 at its bottom end 121.

Figure 59:
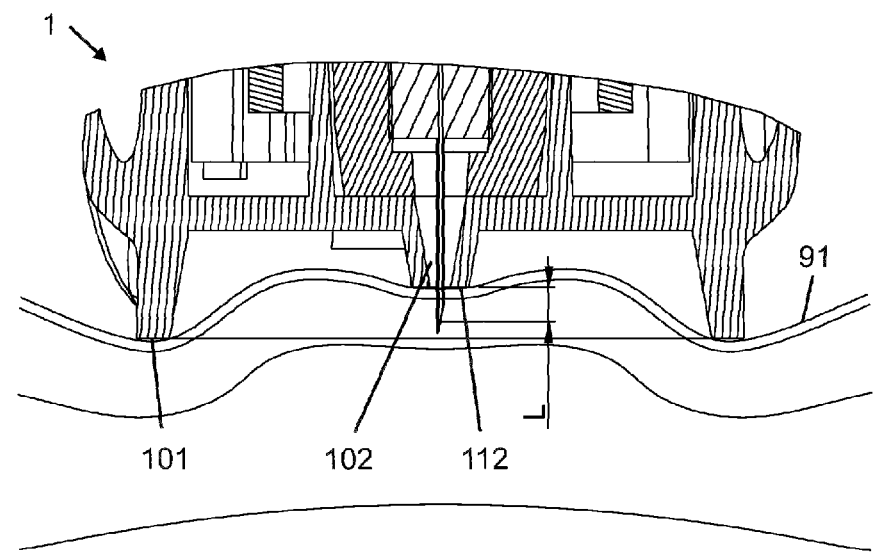
FIG. 59 shows an example of the penetration depth of the needle in the skin.

FIG. 59 shows an example of a device 9 placed on a subject's skin 91. The skin 91 is bended hence stretched, thereby flattening the folds in the skin layers, thus improving puncturing of the skin 91 by the needle 7 and reaching the correct skin depth L. It is noted that both the collar 101 (having a width W11 and diameter D11) as well as a second collar 112 of a small area around the opening 102, rests on the skin 91.

Figure 2:
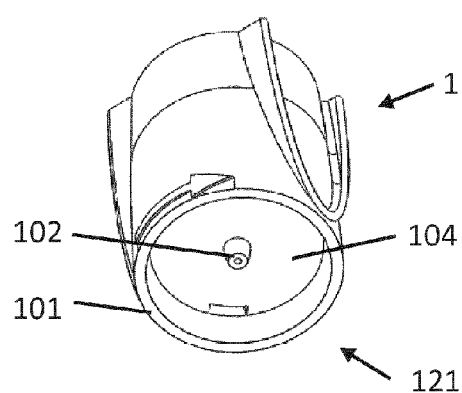
FIG. 2 shows a perspective view of the foot of FIG. 1 from below.

The collar 101 of the embodiment of the foot 1, illustrated in FIG. 2, has e.g. a circular cross section with an inner diameter D11 ranging for example from 6.0 mm to 20.0 mm, e.g. from 8.0 mm to 20.0 mm, for example from 12.0 to 16.0 mm, e.g. about 14.0 mm. The larger the diameter, the more stable the positioning of the foot 1 on the skin, but the more the skin may bend upwards. Very predictable penetration depths (of the needle in the skin) with tolerances smaller than e.g. 0.2 mm have been achieved with a collar diameter D11 of about 14.0 mm. The collar 101 of the foot 1 may have a width W11, as shown in FIG. 3, for example in the range of 0.5 to 3.0 mm, preferably in the range of 1.0 to 3.0 mm, for example 1.5 to 2.5 mm, e.g. about 2.0 mm. Such width reduces or eliminates the risk of accidentally cutting the skin when the foot 1 is placed on a skin. The collar 101 according to embodiments of the present invention may, however, also have a non-circular cross section, e.g. an elliptical cross section, or any other suitable cross section.

Relation to the Needle 7 (Seventh Part)

The collar 101 surrounds an opening 102 in the closing face 104. The opening 102 is adapted so a needle 7 can pass through it, or rather, a first needle end 71 protrude through the opening 102. A needle 7 may be selected such that its dimensions mate with the dimensions of the opening 102, such that the opening can receive the needle 7 and let it protrude. The opening 102 may be funnel-shaped for facilitating reception and passage of such needle 7. The opening 102 has an inner diameter corresponding to the outer diameter of the needle 7, taking into account a limited spacing, e.g. less than 0.8 mm, for example less than 0.4 mm between both. The funnel may e.g. have a diameter ranging from 0.5 mm (bottom end) to 5.0 mm (upper end) and a length ranging from 1.0 mm to 10.0 mm, but other dimensions may also be used. The location of the opening 102 nearby the bent skin (e.g. at a distance less than 2.0 mm from the skin), and the limited spacing between the needle and the opening 102, prevent the needle 7 from bending when penetrating the skin 91. Combined with the stability ensured by the collars 101, 112 (FIG. 59), this allows thin and thin-wall needles to be used, e.g. a needle selected in the range from 26 G to 34 G, thus e.g. 26 G, or 27 G, or 28 G, or 29 G, or 30 G, or 31 G, or 32 G, or 33 G or 34 G, with for example an outer diameter D71 ranging from 0.1842 mm (34 G) to 0.4636 mm (26 G) and a (strictly smaller) inner diameter ranging from 0.0826 mm (34 G) to 0.260 mm (26 G). A thin and short needle helps to reduce the amount of liquid that will remain in the device 9 after administration, and thus helps to reduce the amount of liquid needed.

Relation to the Epidermis

Using thinner needles has the advantage of provoking less pain and smaller wounds and allows accurate administration of fluid at the site of the dermis. By perpendicular positioning of the needle onto the skin, ensured by the collar, the use of thinner needles allows controlling the administration depth more accurately which, in turn, allows administering in thinner epidermis. Thus the device 9 is suited to administer substance to e.g. children and anatomic places where the epidermis is thin.

Relation to the Case 5 (Fifth Part)

Figure 20:
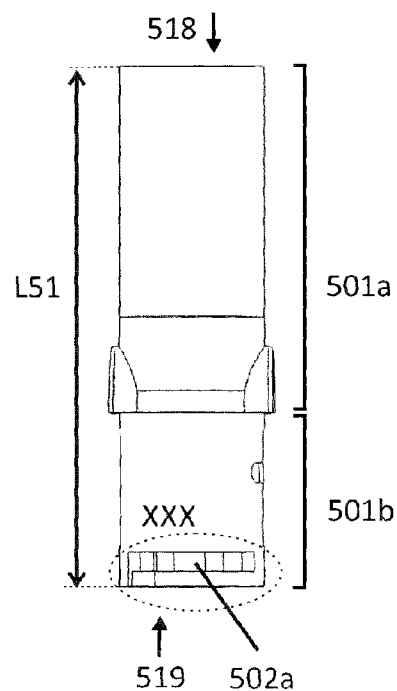
FIG. 20 shows a front view of an embodiment of the case (fifth part) of the device according to embodiments of the present invention.

On the inner wall of the foot 1, at least one pen, for example two or more pens 103 (only one being shown in FIG. 3 and FIG. 4) may be located above the face 104. These pens 103 have a geometrical shape designed for sliding in a corresponding groove 502a, 502b on an outer surface of case 5 (FIG. 20). Each of the pens 103a, 103b may have a bevel 105 on one side to decrease the strength needed to push the pens 103 through the grooves 502 of the case 5. Furthermore the pens may have a bevel 106 on the upper side of the shape to allow the foot 1 to be assembled on the case 5 by snapping over groove 506a during assembly. At the inner side of the wall 111 two grooves 107 are located. These grooves 107 provide the space needed for the snaps 510a, 510b of the case 5 (fifth part) to move outwards, as will be explained further.

Relation to the Needle Hub 2 (Second Part)

Inside the foot 1, one or more extra walls 108 (FIG. 4) may be constructed for the placement of the needle hub 2 (second part). These one or more walls have a height of more than 2.0 mm and are shaped in such a way that they fit around the bulge 202 of the needle hub 2 for angular engagement of the foot 1 and the needle holder 2.

The Needle Hub 2, Also Referred to as the Second Part

Figure 5:
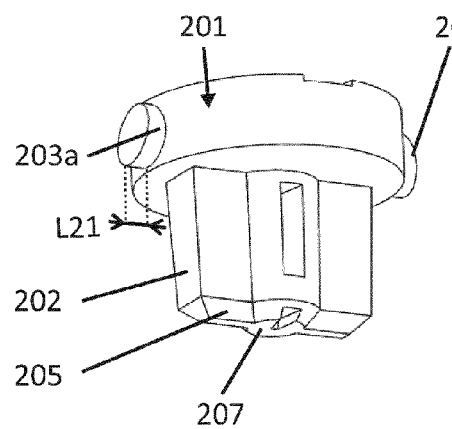
FIG. 5 shows a perspective view of an embodiment of the needle hub (second part) of the device according to embodiments of the present invention, shown from below.

The needle hub 2 (second part) will be explained with reference to FIGS. 5-7. As shown in FIG. 5, the needle hub 2 has a main body 201 and connected thereto a bulge 202. In use, the main body 201 is directed away from the skin, and the bulge 202 is directed towards the skin. At the side of this main body 201 two or more protruding pens 203a, 203b may be provided for engaging with the reservoir 3 (third part) at two or more contact points, as will be explained further in relation to FIG. 11.

Relation to the Foot 1 (First Part)

This bulge 202 is an elongated element to angularly engage the needle hub 2 (second part) with the foot 1 (first part) while allowing axial displacement thereto. Its cross section can be selected from a large variety of shapes, such as e.g. a cylindrical shape with two sidebars, as shown in perspective view in FIGS. 5 and 6 and in cross section in FIG. 7, or a rectangular shape, or any other shape suitable for angular engagement while allowing axial displacement. The shape is chosen such that it fits inside the walls 108 of the foot 1. The bulge 202 has a length L22 of more than 3.0 mm and can have e.g. a conical shape for facilitating the insertion of the needle hub 2 in the foot 1 during assembly, and to ensure a good fit. At the bottom end of the bulge 202 a bevel 205 might be provided to ensure a good guidance into walls 108 during assembly and administration.

Relation to the Reservoir 3 (Third Part)

Figure 6:
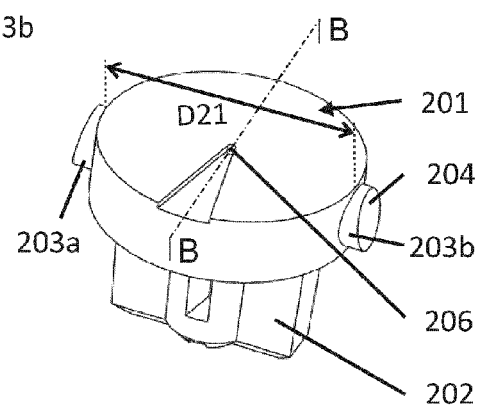
FIG. 6 shows a perspective view of the second part of FIG. 5 from above.
Figure 7:
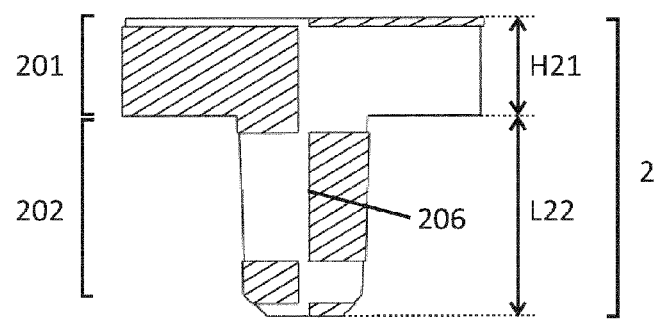
FIG. 7 shows a cross section of the second part of FIG. 6 when cut by plane B-B.
Figure 11:
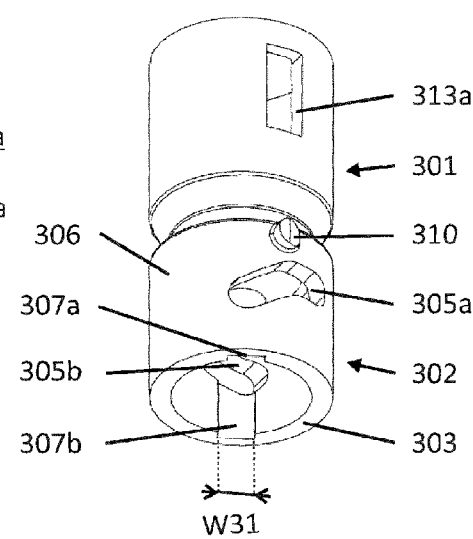
FIG. 11 shows a perspective view of the reservoir of FIG. 8 from below.

The main body 201 can be shaped as an e.g. rounded form, such as a cylindrical shape and can have a diameter D21, as shown in FIG. 6, ranging for example from 4.0 mm to 18.0 mm, such as between 6.0 mm and 12.0 mm, e.g. about 8.4 mm. The height H21 (FIG. 7) of the main body 201 should be at least 1.0 mm for providing sufficient rigidity to the needle hub 2 (second part), and should be less than 8.0 mm for avoiding too much friction when the needle hub 2 is rotated inside the reservoir 3 (during the "unlocking" of the device 9). The height H21 may be e.g. about 2.4 mm. The two or more protruding pens 203a, 203b have a smooth cross section, such as e.g. a circular or an elliptical shape, without sharp edges so as to avoid stress concentration points when the pens 203a, 203b are sliding inside the grooves 305a, 305b provided in the reservoir 3 during rotation of the foot 1. However, a square or rectangular cross section with rounded edges may also work. In case the pens 203a, 203b have a circular cross section, the diameter of the cross section typically ranges for example from 1.0 mm to 5.0 mm, such as between 1.5 mm and 3.0 mm, e.g. about 2.0 mm. The diameter corresponds to the width of the grooves 305a, 305 in the reservoir 3, taking into account a limited spacing, e.g. less than 0.2 mm for allowing easy displacement of the pen 203, and for taking into account any production tolerances. The pens 203a, 203b have a length L21, as shown in FIG. 5, ranging for example from 1.0 mm to 8.0 mm, such as at least 2.0 mm for avoiding decoupling of the pen 203 from the groove 305, and preferably less than 6.0 mm for keeping the diameter D91 of the assembled device 9 as small as possible. The pens 203 may have a bevel 204 (FIG. 6) on their outer rim for allowing easy insertion of the pen 203 into the groove 305 (via groove 307) during assembly (FIG. 11).

The Reservoir 3, Also Referred to as the Third Part

Figure 8:
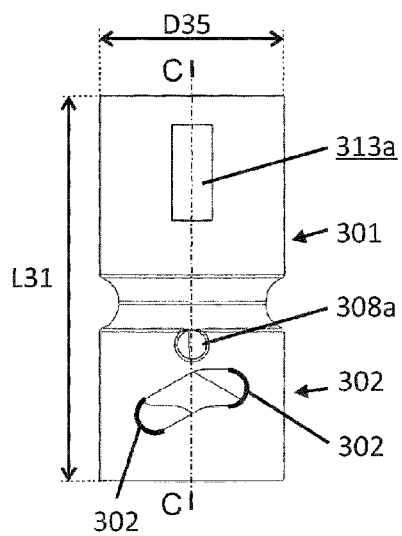
FIG. 8 shows a front view of an embodiment of the reservoir (third part) of the device according to embodiments of the present invention.
Figure 12:
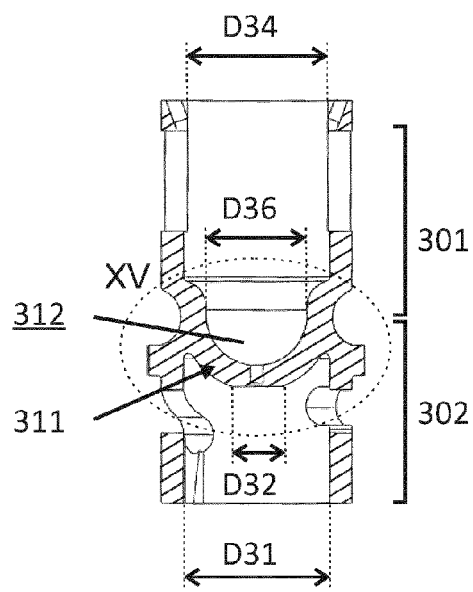
FIG. 12 shows a front view of the cross section of the reservoir of FIG. 8 when cut by plane C-C. An internal wall thereof forms the "actual reservoir" for holding a fluid.

The reservoir 3 (third part) will be explained with reference to FIGS. 8-16. A frontal view is shown in FIG. 8. It comprises an element with a tubular shape comprising a first and a second hollow segment 301, 302 connected together, and separated from each other by an inner dividing wall 311 (FIG. 12). In an embodiment, the first and second segments 301, 302 may have roughly the same size (e.g. diameter and length). The reservoir 3 is adapted to be positioned into the case 5 (fifth part), so that the second segment 302 is directed towards the foot 1 (first part), and when assembled, the first segment 301 is directed towards the plunger 6 (sixth part). The dividing wall 311 may be smooth shaped without sharp edges or protruding elements so that it can contain a liquid at the side of the first hollow segment 301, in particular for example a liquid drug. The dividing wall 311 forms a bottom of a hollow space 312. The hollow space 312 may have a boundary that is a surface of revolution. In cross section it may have a geometrical shape without sharp edges, for example a shape which is part of a circle or ellipse or parabola. However part of a square or rectangular cross section may also be used.

Relation Between the Reservoir 3 (Third Part) and the Foot 1 (First Part)

The reservoir 3, also referred to as the third part, has a length L31, as shown in FIG. 8, ranging for example from 12.0 mm to 40.0 mm, e.g. 23.0 mm. In particular embodiments, this length L31 ranges from 20.0 mm to 30.0 mm to limit the total length L91 of the assembled device 9 to a predetermined range, thereby taking into account the length and coupling of the other parts. When administering the liquid, e.g. drugs, to a subject, the distal surface 303 (FIG. 11) of the second segment 302 comes into contact with the inner face 104 of the foot 1 (first part). The length L31 of the reservoir 3 (third part) is one of the parameters defining the depth that the needle 7 (seventh part) will enter into the skin of a subject.

Relation Between the Reservoir 3 (Third Part) and the Needle Hub 2 (Second Part)

Figure 9:
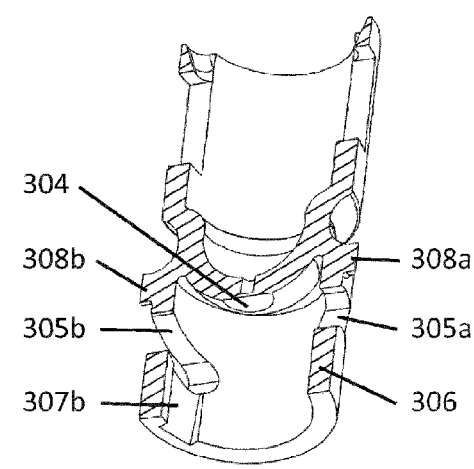
FIG. 9 shows a perspective view of the right fraction of the reservoir of FIG. 8 when cut by plane C-C.
Figure 10:
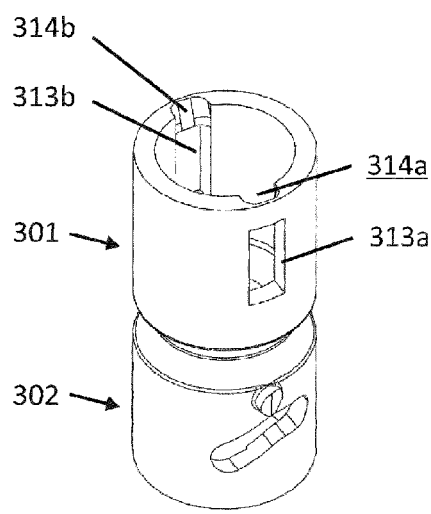
FIG. 10 shows a perspective view of the reservoir of FIG. 8 from above.
Figure 13:
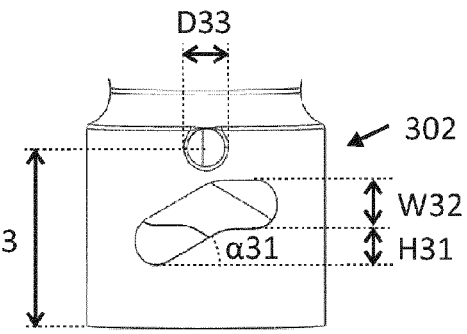
FIG. 13 shows the lower part of the reservoir of FIG. 8.

The tubular shape of the second segment 302 of the reservoir 3 has an inner diameter D31, as shown in FIG. 12, ranging for example from 5.0 mm to 18.0 mm, such as between 7.0 mm and 12.0 mm, e.g. about 8.7 mm. The inner diameter D31 corresponds to the outer diameter D21 (FIG. 6) of the needle hub 2, taking into account a small spacing between the reservoir 3 and the needle hub 2, e.g. less than 0.2 mm to allow easy displacement of the needle hub 2 within the reservoir 3 during assembly, activation and administration, i.e. allowing respectively longitudinal translation and rotation of the needle hub 2 in the reservoir 3, and to take into account any production tolerances. A surface 304 (FIG. 9) of the dividing wall 311 located near the bottom of hollow space 312 but at the side of the dividing wall facing the foot 1, acts as a contact and reference plane for the main body 201. It will be penetrated by the second needle end 72 during activation. The surface 304 has a diameter D32, as shown in FIG. 12, of at least 1.0 mm, e.g. 1.8 mm, to provide a sufficiently large contact area with the needle hub 2 when administering the liquid, e.g. a drug. Two or more grooves 305a, 305b may be provided in the wall 306 of segment 302. These grooves 305a, 305b have a width W32, as shown in FIG. 13, ranging from 1.0 mm to 8.0 mm, e.g. about 1.5 mm. This width W32 corresponds to the diameter of the pens 203a, 203b of the needle hub 2, taking into account a small spacing, e.g. less than 0.40 mm, to allow easy displacement of the pens 203 of the needle hub 2 in the grooves 305 of the reservoir 3, and to take into account any production tolerances. Ideally, the spacing is less than 0.2 mm to avoid unwanted movement of the needle hub 2 inside the reservoir 3. These grooves 305 are designed to mount the needle hub 2 to the reservoir 3, and thus to indirectly mount the needle hub 2 to the case 5. The grooves 305a, 305b are inclined with an inclination angle α31 with respect to a plane perpendicular to the longitudinal axis of the device 9, so that a rotation of the foot 1 results in a longitudinal displacement of the needle hub 2 in the reservoir 3 during activation. The inclination angle α31 may be an angle in the range of 5.0° to 60.0° (see FIG. 13). The inclination angle α31 may for example be larger than 45.0° so that a limited rotation angle of the foot (e.g. over an angle of 60.0°) results in sufficient axial displacement of the needle hub 2, e.g. sufficient for penetrating the cavity 315 located at a bottom of the hollow space 312 (see FIG. 15). An inclination angle α31 smaller than 45.0° (e.g. about 20° or about 30° or about 40°) would also work, but would require a larger rotation angle of the foot 1 around its longitudinal axis during activation. The grooves 305 may have rounded ends 309 (indicated in thicker line in FIG. 8 for illustrative purposes). The grooves 305a, 305b can have a height H31, as shown in FIG. 13, ranging for example from 1.0 mm to 10.0 mm, e.g. 2.0 mm, corresponding to the axial displacement of the needle hub 2 for penetrating the dividing wall 311 (during activation of the device 9). This height H31 may be more than 1.0 mm to avoid premature contact between the needle 7 and the reservoir 3, e.g. caused due to packaging or transport, and less than 3.0 mm to limit the total length L91 of the assembled device 9, and/or to reduce the amount of liquid which is spilled or left behind in the needle. Two or more grooves 307a, 307b (FIG. 11) may be provided on an inner surface of the wall 306 to allow the assembly of the needle hub 2 into the reservoir 3. These grooves 307a, 307b have a width W31, as shown in FIG. 11, ranging for example from 1.0 mm to 5.0 mm, e.g. 1.5 mm, and a non-constant depth (FIG. 9). The width W31 corresponds to the diameter of the circular cross section of the pens 203a, 203b, taking into account a small spacing, e.g. less than 0.2 mm to allow an easy assembly of the needle hub 2 into the reservoir 3, and to take into account any production tolerances. The surface of the grooves 307a, 307b may have an inclination (see FIG. 9) corresponding to an varying depth of the groove, to further facilitate the assembly of the needle hub 2 into the reservoir 3. This inclination may have an angle, not shown, ranging for example from 1.0° to 35.0°, such as between 1.0° and 20.0°, e.g. 5.0°. The decreasing depth of the grooves 307 (FIG. 9), in combination with the shape of the bevel 204 (smaller diameter on an upper side, and larger diameter on a lower side) provide for easy insertion of the pens 203 into the grooves 307, and for locking them into the grooves 305, so that the needle hub 2 is locked to the reservoir 3 (during assembly).

Relation Between the Reservoir 3 (Third Part) and the Seal 4 (Fourth Part)

The first segment 301 of the reservoir 3 (third part) has an inner diameter D34, as shown in FIG. 12, ranging for example from 5.0 mm to 18.0 mm, such as between 7.0 mm and 12.0 mm, e.g. about 8.7 mm. The inner diameter D34 is slightly smaller than the outer diameter D41 (FIG. 18) of the seal 4 (also referred to as the fourth part), e.g. 0.10 to 0.40 mm smaller, for clamping the seal 4 (fourth part) into the first segment 301 of the reservoir 3 and ensure fixation during assembly and administration. The first segment 301 of the reservoir 3 may have a carrier groove surface (not shown) located at the inner enclosed volume to allow easier positioning of the seal 4, e.g. a circumferential groove having a width corresponding to the height of the seal 4, and a depth suitable for clamping the seal 4.

Relation Between the Reservoir 3 (Third Part) and the Case 5 (Fifth Part)

Figure 14:
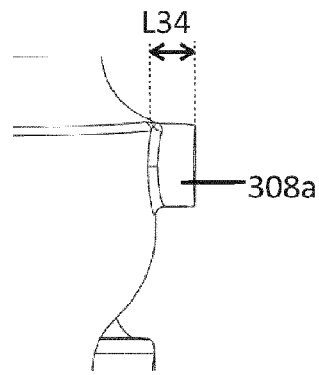
FIG. 14 shows a close-up of a side view of the reservoir.
Figure 28:
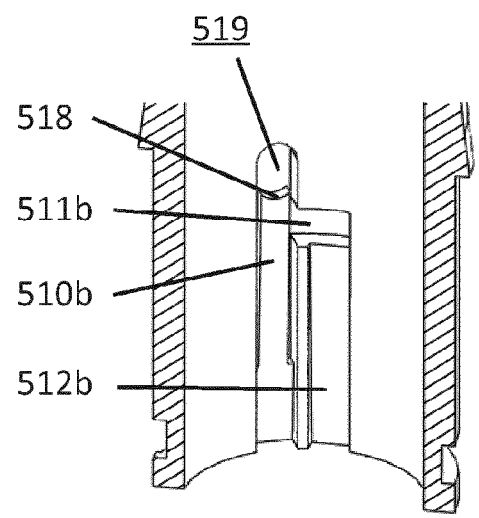
FIG. 28 shows a perspective view of a close-up of the case of FIG. 24.
Figure 29:
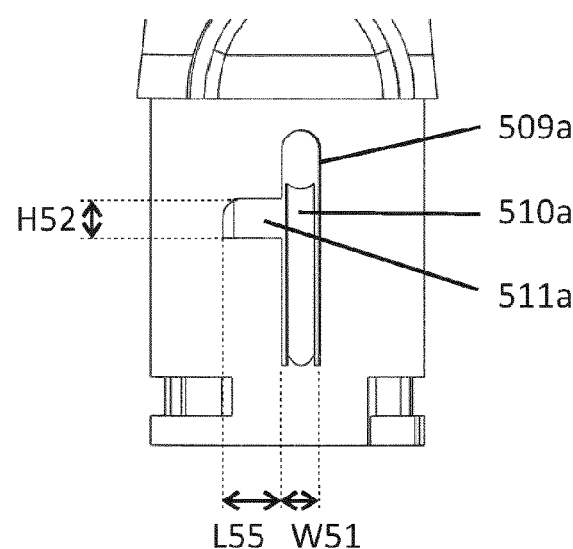
FIG. 29 shows a side view of a close-up of the case of FIG. 21.
Figure 61:
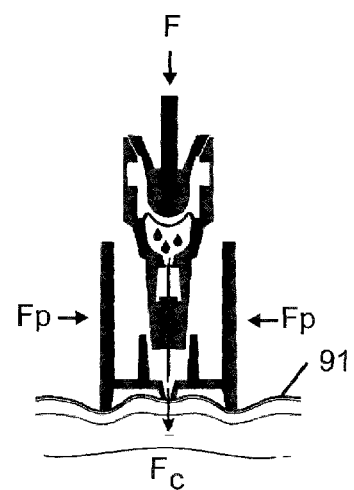
FIG. 61 shows the schematic representation of FIG. 60 when a force is applied to the plunger, and the plunger has made an initial movement towards the reservoir, while no pressure is exerted on the fluid yet.

The reservoir 3 has an outer diameter D35, as shown in FIG. 8, ranging for example from 6.5 mm to 24.0 mm, for example between 9.0 mm and 14.0 mm, e.g. 11.3 mm, to limit the total outer diameter D91 of the assembled device 9, for it should be easy to handle e.g. to hold firmly between the operator's thumb and middle finger, for exerting an inwardly directed force Fp (FIG. 61). Two or more protruding pens 308a, 308b may be provided on the outer face of the reservoir 3. These pens 308a, 308b can be located on the outer face of the first segment 301 or of the second segment 302. The centres of the pens 308a, 308b are located at a distance L33 from the distal surface 303, as shown in FIG. 13. In exemplary embodiments, this distance L33 is about half of the length L31 of the reservoir 3. The two or more pens 308a, 308b may have a cross section without sharp edges, such as e.g. a circular or an elliptical shape, so as to avoid stress concentration points when the pens 308a, 308b are rotated inside openings 511a, 511b (FIG. 28) provided in the case 5 during activation of the device 9. However, a square or rectangular cross section with rounded edges may also work. In case the pens 308a, 308b have a circular cross section, the diameter D33 of the cross section (see FIG. 13) typically ranges from 1.0 mm to 5.0 mm, for example between 1.5 mm and 3.0 mm, e.g. about 1.8 mm. The diameter D33 corresponds to the width W51 of groove 509 (FIG. 29) in the case 5, taking into account a small spacing, e.g. less than 0.2 mm for allowing easy displacement of the pen, and for taking into account any production tolerances. The pens 308a, 308b have a length L34, as shown in FIG. 14, ranging for example from 1.0 mm to 8.0 mm, such as at least 2.0 mm for avoiding decoupling of the pen 308a, 308b from the opening/groove 509 especially after use of the device 9, for fixating the pens 308a, 308b on the top 518 of the snaps 510a, 510b thereby preventing that the needle 7 is accessible, and preferably less than 6.0 mm for keeping the outer diameter D91 of the assembled device 9 within the desired range of 15.0 mm to 50.0 mm. The pens 308 may have a bevel 310 (FIG. 11) on their outer rim for pushing the snaps 510 outwardly as the pens 308 are being moved from a position in the circumferential slots 511 to a position in the longitudinal grooves 509 during activation of the device 9, when the foot 1 and along with it the reservoir 3 are being rotated. This allows easy insertion of the pens 308 into the grooves 509 (FIG. 28, FIG. 29).

Relation Between the Reservoir 3 (Third Part) and the Plunger 6 (Sixth Part)

Figure 4:
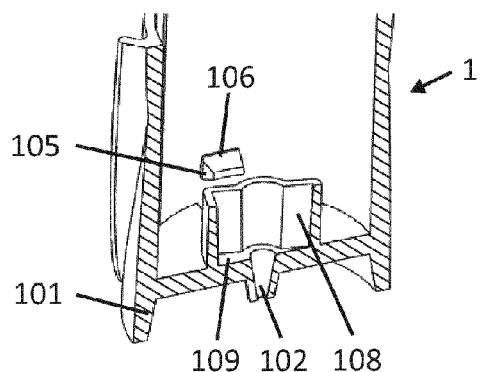
FIG. 4 shows the rear fraction of the foot of FIG. 3, slightly enlarged and from a slightly different angle.
Figure 16:
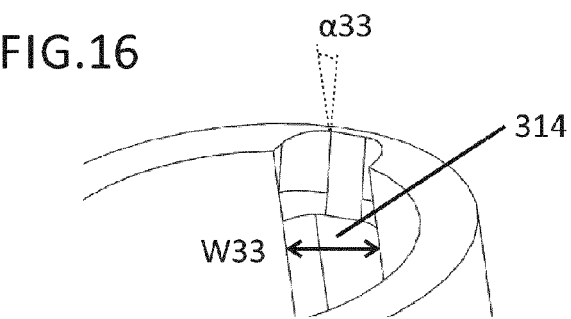
FIG. 16 shows a perspective view of a close-up of the reservoir of FIG. 10.
Figure 62:
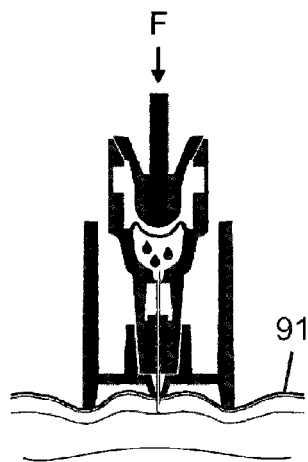
FIG. 62 shows the schematic representation of FIG. 61, when a force is applied to the plunger, and the reservoir has moved down until it rests on the bottom of the foot, and the needle has penetrated the skin, while no pressure is exerted on the fluid yet.

In case the hollow space 312 formed by the dividing wall 311 (FIG. 12) takes the form of a revolution of a half sphere, it may have an inner diameter D36 ranging for example from 2.0 mm to 8.0 mm (see FIG. 12). This diameter D36 may for example range between 3.0 mm and 4.0 mm, e.g. 3.5 mm so as to keep the length L92 and diameter D91 ratio of the assembled device 9 as ergonomically as possible and for optimal effect of stretching the skin by the outer collar 101 (FIG. 4). The inner diameter D36 corresponds to the outer diameter D61 of the plunger head 603 (FIG. 32), taking into account a limited spacing in between them, e.g. less than 0.40 mm to allow an easy displacement of the head 603 of the plunger 6 into the hollow (or substantially filled with liquid) space 312, with sufficient space provided for the wall thickness of the seal 4 to be clamped between the dividing wall 311 and the plunger head 603, and to take into account any production tolerances. The hollow space 312 can contain the fluid (e.g. vaccine) and encloses a predefined volume in the range of 0.01 ml to 1.0 ml, e.g. in the range of 0.1 to 0.5 ml, e.g. about 0.1 ml, e.g. to ensure optimal effect of the fluid, e.g. drug. This amount can easily be set by choosing appropriate dimensions of the dividing wall 311 (and optionally plunger head 603). Thus different embodiments of the device may have different volumes of the "actual reservoir". Alternatively or in combination thereto, the size and/or dimensions of the seal 4 may vary depending on the amount of fluid to be stored. The head of the plunger 603 has a shape which is complementary to the shape of the bottom of the space 312, taking into account the thickness of the seal 4 in between, so that substantially no fluid remains in the reservoir after administration. The surface of the flexible seal 402 may, clamped in between in stretched form, take account of a tolerance of e.g. less than 0.4 mm between the inner diameter D36 (FIG. 12) of the bottom of the hollow space 312 and the outer diameter D61 (FIG. 32) of the plunger head 603. Two or more openings 313a, 313b (FIG. 10) may be provided in the wall 306. The two or more openings 313a, 313b correspond to the form of snap heads 605a, 605b (FIG. 33) taking into account a small spacing, e.g. 0.2 mm so as to allow an easy displacement of the snap heads 605a, 605b into the area of the openings 313a, 313b provided. Grooves 314a, 314b provide an access for the snap heads 605a, 605b towards the openings 313. The grooves 314a, 314b have a width W33, as shown in FIG. 16, ranging from 1.0 mm to 6.0 mm, e.g. 1.8 mm. This width W33 corresponds to the width W61 of the snap heads 605a, 605b, taking into account a limited spacing, e.g. less than 0.2 mm to allow easy displacement of the plunger 6, and to take into account any production tolerances. The grooves 314a, 314b may have an inclination over their entire length, or only a portion thereof. This inclination may include an angle α33 with respect to the inner surface of the first segment 301, as shown in FIG. 16, ranging for example from 0.0° to 50.0°, such as between 20.0° and 40.0°, e.g. 30.0° to ensure that a sufficiently large force, e.g. a force larger than a predefined threshold value selected from the range of 0.5 to 30 Newton, has to be applied on the plunger surface 607 before the snap heads 605a, 605b slide through the grooves 314a, 314b and into the openings 313a, 313b. The predefined threshold value may e.g. be about 0.5 N, or about 1.0 N, or about 1.5 N, or about 2.0 N, or about 2.5 N, or about 3.0 N, or about 3.5 N, or about 4.0 N, or about 4.5 N, or about 5 N, or about 6 N, or about 7 N, or about 8 N, or about 9 N, or about 10 N, or about 12 N, or about 14 N, or about 16 N, or about 18 N, or about 20 N, or about 22 N, or about 24 N, or about 26 N, or about 28 N, or about 30 N. According to an aspect of the present invention, the force required to move the plunger 6 so as to engage with the reservoir 3—in the embodiment shown i.e. the force required to move the snap heads 605 (FIG. 33) into the grooves 314 (FIG. 53) against the friction or resistance provided by the grooves 314 in contact with the snap heads 605 (called second friction or resistance)—must be at least the force required to move the reservoir 3 with respect to the case 5 against the friction or resistance provided by the snaps 510 in contact with the pens 308 of the reservoir 3 (called first friction) enlarged with the maximal force to penetrate the subject's skin, e.g. enlarged with 0.5 Newton. This choice is to prevent locking by the movement of the snap heads 605 into the grooves 313 prior to penetrating the subject's skin. The friction or resistance between the snap heads 605 and the grooves 314 is function of the relative position of the plunger 6 in the reservoir 3 (called dynamic second friction). The dynamic second friction can e.g. be determined by choosing an appropriate material of the snap heads 605, and/or appropriate dimensions of the snap heads 605, and/or shape of the snap heads 605, and/or surface finishing of the snap heads 605, and/or material of the reservoir 3, and/or dimensions of the grooves 314, and/or surface finishing of the grooves 314. The second friction is predetermined such that penetration of the subject's skin 91 to the desired depth L is achieved before the plunger head 603 touches/hits the seal 4 in the reservoir 3 to ensure that no fluid is squeezed out of the actual reservoir 312 before proper penetration of the subject's skin (FIG. 62). Of course, this friction/resistance is to be measured when the device 9 is in unlocked mode, also called activated mode.

In an embodiment, the angle α33 between the groove 314 and the axis of the device 9 measured at the entrance of the groove 314, is used as a parameter for controlling the (second) friction between the reservoir 3 and the plunger 6.

By assigning an appropriate value to angle α33, e.g. 30.0°, it can be ensured that (for given materials and dimensions and shapes of the parts) the force required to overcome the friction/resistance between the plunger 6 and the reservoir 3 is at least a predetermined value, e.g. 0.5 Newton larger than the force required to overcome the friction/resistance between the reservoir 3 and the case 5 (more in particular, between the snaps 510 and the pens 308). For given dimensions and shapes of the parts, the skilled person can easily determine the angle α33, for example by trial and error.

The predetermined threshold value of at least 0.5 Newton is selected to be sufficiently high to overcome the force required to introduce the first needle end 71 into the subject's skin.

This ensures, when the device 9 is in activated mode, and when a force is applied to the plunger surface 607 (and directed towards the opening 102), that first the reservoir (and along with it the needle hub 2 and the needle 7) is moved within the case 5 and that the needle 7 is penetrated into the skin, and that only thereafter the plunger 6 is moved with respect to the reservoir 3 for exerting pressure on the liquid. In other words, by ensuring that the second friction is at least the predetermined amount (e.g. at least 0.5 Newton) higher than the first friction, it is ensured that the needle 7 is penetrated into the skin before pressure is exerted upon the liquid in the reservoir. In this way spilling of the vaccine is reduced/avoided. The friction between the reservoir 3 and the plunger 6 should however not be as large so as to prevent the displacement of the plunger 6 with respect to the reservoir 3 altogether, when a force is applied by the operator. The corners of the grooves 314a, 314b may be rounded so as to avoid stress concentration points.

It is noted that the force needed to make the second needle end 72 penetrate the wall section 316, is exerted by rotating the foot 1 during activation of the device 9, and not by pressing the plunger 6. Hence the force required for penetrating the needle into the reservoir 3 (during activation of the device 9) can be chosen independent of the friction described in the previous paragraphs.

Relation Between the Reservoir 3 (Third Part) and the Needle 7 (Seventh Part)

Figure 15:
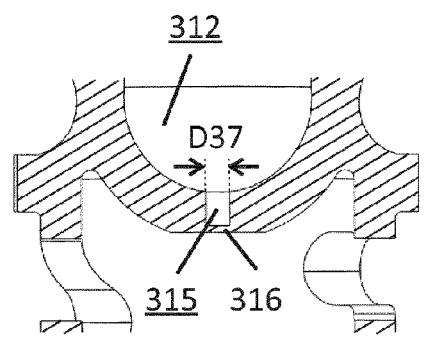
FIG. 15 shows a close-up of the "actual reservoir" of FIG. 12.

Inside the dividing wall 311 of the reservoir 3 (third part), for example in the centre thereof, a cavity 315 (FIG. 15) is provided, via which the second end 72 of the needle 7 (seventh part) can get access to the space 312 for transporting the fluid from the reservoir 3 to the subject (e.g. patient) during use of the device 9. This cavity 315 may have e.g. a cylindrical or conical shape. In the latter case the smaller diameter may be directed towards the foot 1 for guiding the needle 7. The dimension of the cavity 315 should be large enough so as to allow sufficient space for the second end 72 of the needle 7 to enter the cavity 315, but small enough so as to ensure a minimal volume of space lost as overfill. In case the cavity 315 has a cylindrical shape (as shown in FIG. 15), it may have a diameter D37 ranging for example from 0.4 mm to 4.0 mm, such as between 0.4 mm and 1.0 mm. In an embodiment, the cavity 315 has a diameter of 0.75 mm enabling penetration of a needle having a size in the range of 26 G to 34 G with e.g. an outer diameter D71 ranging from 0.1842 mm (34 G) to 0.4636 mm (26 G) and a (strictly smaller) inner diameter ranging from 0.0826 mm (34 G) to 0.260 mm (26 G). Between the surface 304 (FIG. 9) and the cavity 315 a wall section 316 may be provided with a thickness ranging for example from 0.1 mm to 0.5 mm, e.g. about 0.2 mm. This wall section 316 should be soft enough to allow penetration by the second needle end 72 of the needle 7. The material of the reservoir 3 may have a Young's modulus ranging for example from 500 to 3000 MPa, e.g. about 1700 MPa. The reservoir 3 can be constructed from a polymer, e.g. polypropylene.

The hollow space 312 could also be loaded with a separate capsule, e.g. a capsule containing a fluid, e.g. vaccine, in which case cavity 315 may be a through hole, rather than a blind hole. Such a capsule could be constructed out of a variety of materials, e.g. polymers, aluminium.

The Seal 4, Also Referred to as the Fourth Part

Figure 17:
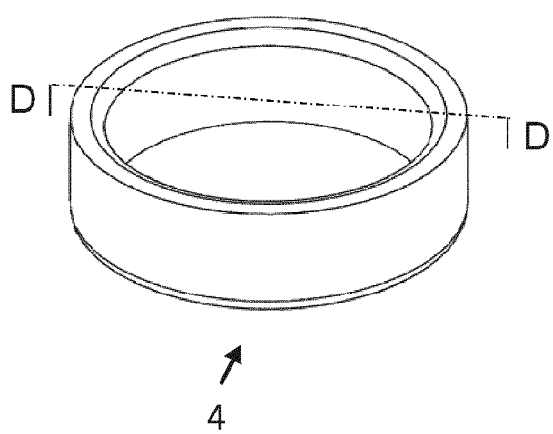
FIG. 17 shows a perspective view of a first embodiment of the seal (fourth part) of the device according to embodiments of the present invention, shown from above.

The seal 4, also referred to as the fourth part, will be explained with reference to FIGS. 17-19. Its function is to close the reservoir 3 (third part) after fluid (e.g. drug or vaccine) has been added in the hollow space 312, and to ensure that no or only a minimal amount of fluid remains in the device 9 after administering thereof. The seal 4 may have a hollow cylindrical or another bulged or curved form with a circular cross section, that is closed at one end with an end portion 402, corresponding to the inner form of 301 and the top surface of the hollow space 312. The seal 4 may comprise or consist of a flexible or elastic material, e.g. rubber, so as to be able to take the form of the space 312 when the plunger head 603 is pressed towards the bottom of the space 312 when administering the fluid.

Relation Between the Seal 4 (Fourth Part) and the Reservoir 3 (Third Part)

Figure 18:
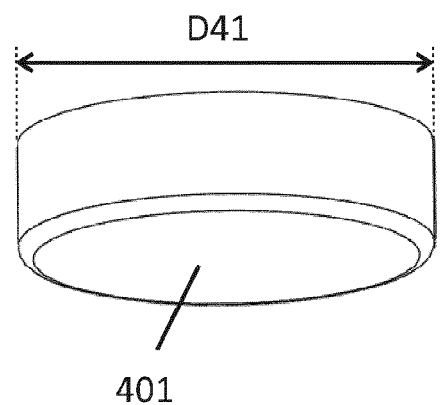
FIG. 18 shows a perspective view of the seal of FIG. 17 from below.

In the embodiment shown in FIG. 18, the seal 4 has an outer diameter D41, corresponding to the inner diameter D34 of the first segment 301 of the reservoir 3. In an embodiment the diameter ranges from 5.2 mm to 18.2 mm, for example between 7.2 mm and 12.2 mm, e.g. about 8.9 mm. The outer diameter D41 of the seal 4 may be slightly smaller than the inner diameter D34 of the first segment 301 of the reservoir 3, e.g. in the range of 0.10 mm to 0.40 mm smaller, e.g. about 0.2 mm smaller, for clamping the seal 4 into the first segment 301 of the reservoir 3 and ensuring fixation during assembly and use. To that end, the first segment 301 of the reservoir 3 may have a carrier groove (not shown) for defining the inner volume 312 to allow easier positioning of the seal 4. This groove may be e.g. a circumferential groove having a width (in longitudinal direction of the device) corresponding to the height of the seal 4, and a depth (in radial dimension of the device) suitable for clamping the seal 4.

Relation Between the Seal 4 (Fourth Part) and the Plunger 6 (Sixth Part)

Figure 19:
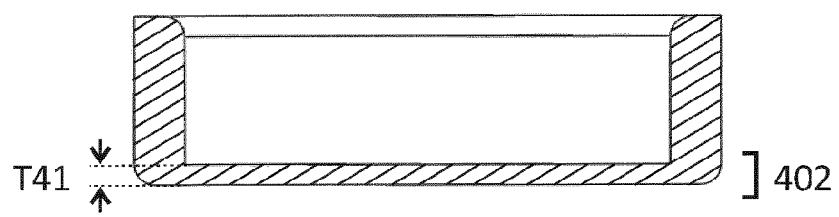
FIG. 19 shows a front view of the cross section of the seal of FIG. 17 when cut by plane D-D.
Figure 57:
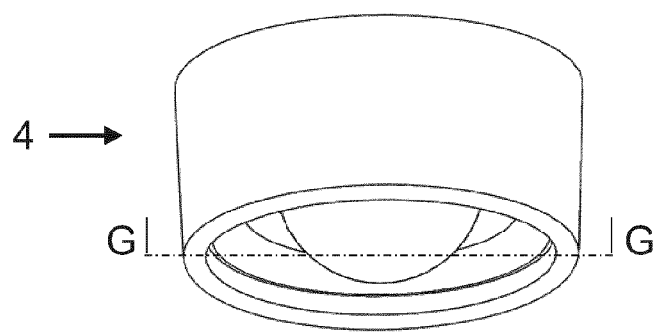
FIG. 57 shows a perspective view of a second embodiment of the seal (fourth part) of the device according to embodiments of the present invention, shown from below.
Figure 58:
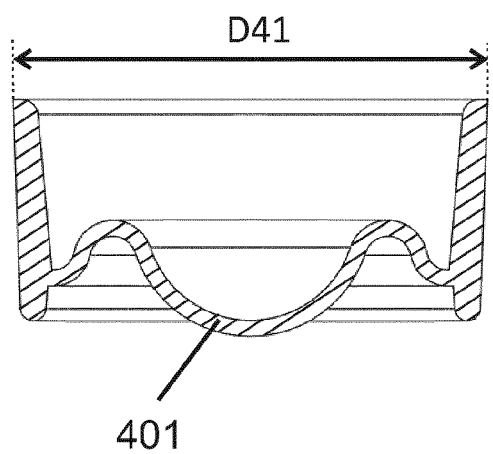
FIG. 58 shows a front view of the cross section of the seal of FIG. 57 when cut by plane G-G.

The end portion 402 of the seal 4 has a thickness T41, as shown in FIG. 19, ranging for example from 0.1 mm to 2.5 mm, e.g. about 0.4 mm to ensure maximal flexibility to attain the form of the plunger head 603, when being squeezed between the plunger head 603 and the bottom of the space 312. The end portion 402 may have a flat shape (as illustrated in FIG. 18), or may have a preformed shape, e.g. a bulge shape (as shown in FIGS. 57 and 58), e.g. a semi-spherical or dome-shape, for increasing the surface area of the end portion 402 when at rest. This increase in surface area of the end portion 402 of the seal 4 reduces the stretch needed for applying the seal 4 to the bottom of the hollow space 312 by means of the plunger head 603. The seal 4 may be placed with its concave side towards the (hollow/filled) space 312.

The Case 5, Also Referred to as the Fifth Part

The case 5, also referred to as the fifth part, will be explained with reference to FIGS. 20-31. As shown in FIG. 20 in front view and FIG. 23 in perspective view, the case 5 may have a hollow tubular shape, e.g. a substantially cylindrical or conical tubular shape, delimited by a wall having a first segment 501a for cooperating with the spring 8 (eighth part), the plunger 6 (sixth part) and the reservoir 3 (third part), and a second segment 501b for cooperating with the foot 1 (first part) and the reservoir 3. The case 5 has a total length L51, as shown in FIG. 20, ranging for example between 15.0 mm and 110.0 mm, such as between 40.0 mm and 60.0 mm, e.g. about 53.0 mm, so that the device 9 can be firmly held in a human hand, and to ensure an ergonomic form of the device 9.

Relation Between the Case 5 (Fifth Part) and the Foot 1 (First Part)

Figure 21:
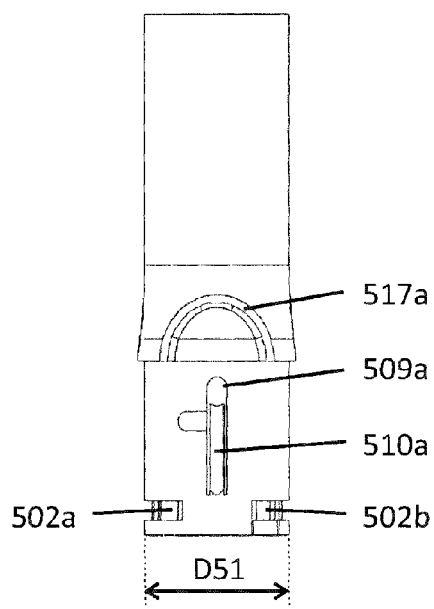
FIG. 21 shows a side view of the case of FIG. 20.
Figure 22:
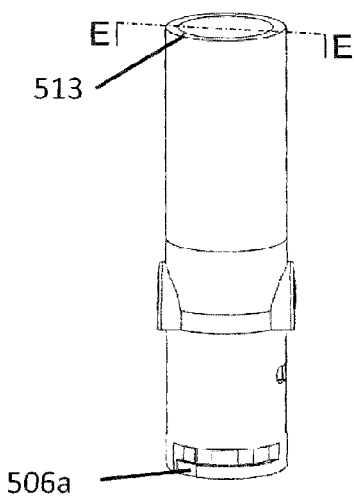
FIG. 22 shows a perspective view of the case of FIG. 20 from above.
Figure 24:
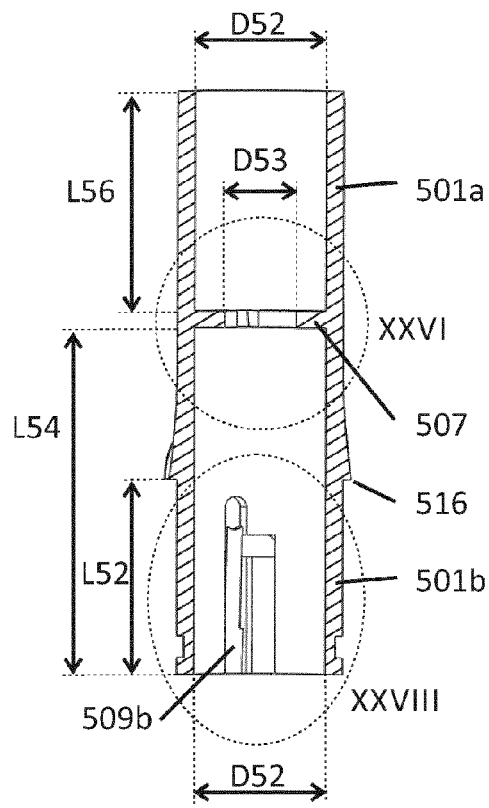
FIG. 24 shows a front view of the cross section of the case of FIG. 20 when cut by plane E-E.

The second segment 501b has a length L52, as shown in FIG. 24, ranging for example between 6.0 mm and 35.0 mm, e.g. about 17.7 mm. This length L52 corresponds to the length L11 (from the top to the pen 103) of the foot 1, but may be slightly larger for taking into account a small spacing, e.g. about 0.10 mm to take into account any production tolerances. In case the case 5 has a cylindrical tubular shape, the wall 501b has an outer diameter D51, as shown in FIG. 21, ranging for example from 10.0 mm to 25.0 mm, for example less than 18.0 mm (to limit the diameter D91 of the assembled device 9), e.g. about 15.0 mm. The outer diameter D51 of the wall 501b corresponds to the inner diameter D11 of the foot 1, taking into account a limited spacing, e.g. less than about 0.2 mm to allow easy displacement of the foot 1 with respect to the case 5, and to take into account any production tolerances. The case 5 may have one or more first grooves, e.g. two grooves 502a, 502b (FIG. 20), located on the outer surface of the wall 501b, and having a circumferential portion lying substantially in a plane perpendicular to the longitudinal axis of the case 5, and having an insertion portion 506 for allowing insertion of the pens 103 of the foot 1. In the embodiment shown in FIG. 30, the first grooves 502a, 502b have an L-shape, the short leg of the "L" being the insertion portion 506, the long leg of the "L" being the circumferential portion.

Figure 30:
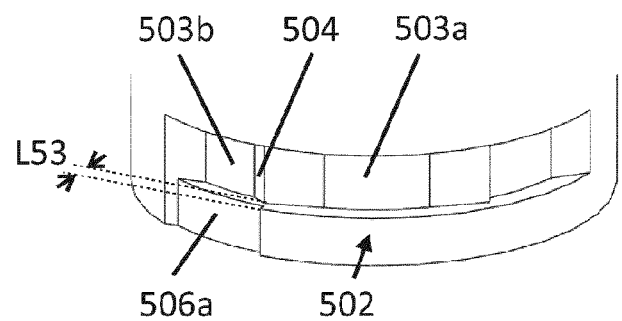
FIG. 30 shows a perspective view of a close-up of the case of FIG. 20.
Figure 31:
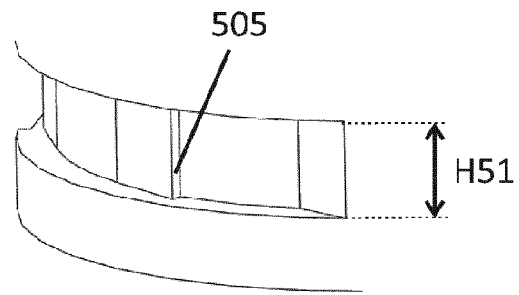
FIG. 31 shows a perspective view of a close-up of the case of FIG. 20.

The circumferential portion of the first grooves 502 will be described first. The first grooves 502a, 502b have a shape suitable for allowing insertion of the pens 103a, 103b therein (during assembly of the device 9). The first groove 502 may have e.g. a rectangular cross section in a plane that contains the longitudinal axis of the case 5. The dimensions of the first grooves 502a, 502b correspond to the dimensions of the pens 103a, 103b, e.g. the first grooves 502 have a height H51, as shown in FIG. 31, ranging for example between 0.6 mm and 5.0 mm, e.g. about 2.0 mm. The first grooves 502a, 502b may contain two or more different levels, e.g. an upper level 503a and a lower level. With "level" is meant a varying distance of the inner surface of the groove 502 to the longitudinal axis of the case 5. These different levels 503a, 503b provide a varying amount of resistance when the pens 103a, 103b of the foot 1 are moved along the grooves 502a, 502b when the foot 1 is rotated with respect of the case 5 during the activation phase of the device 9. The difference between the different levels 503a, 503b, i.e. the difference in radius with regard to the longitudinal axis can e.g. be a distance L53 as shown in FIG. 30, of less than 1.0 mm, for example less than 0.5 mm, e.g. 0.3 mm. Between the upper level 503a and the lower level 503b, a bevel 504 may be provided. This bevel 504 provides a smooth transition from the upper level 503a to the lower level 503b, thus facilitating movement of the foot 1 with respect to the case 5, while at the same time providing a tactile and auditory feedback to the user, each time the pens 103 pass the at least one bevel 504, for indicating that the device 9 is being activated. One or more extended ribs, e.g. one extended rib 505, may be constructed in the first grooves 502a, 502b. This extended rib 505 may have a bevel on one side and a sharp edge on the other, as shown in FIG. 31, so as to function as a hook for blocking return movement and hence at the same time providing tactile feedback to the operator that the device 9 is in activation stage when the foot 1 has been rotated over the full activation angle, i.e. when the pens 103a, 103b of the foot 1 have reached their end position in the grooves 502.

The first grooves 502 also have an insertion portion 506a, 506b (the short leg of the "L") running substantially in parallel to the longitudinal axis, for allowing access to the pens 103a, 103b through which they can be inserted into the first grooves 502a, 502b. On the outer surface of the wall 501a of the first segment or of the wall 501b of the second segment a circumferential edge, e.g. an edge with a smooth inclination 516 (FIG. 24), may be provided. This edge 516 may provide a smooth transition of the outer surface of the device 9, from the upper part of the case 501a to the foot 1 (when assembled on the case 5). On the outside of the wall 501a or wall 501b, two or more protrusions 517a, 517b (FIG. 25) may be constructed to provide an improved support for finger placement. These protrusions 517a, 517b may be designed so that they align with the protrusions 109 on the foot 1 when the activation of the device 9 is complete.

Relation Between the Case 5 (Fifth Part) and the Reservoir 3 (Third Part)

Figure 23:
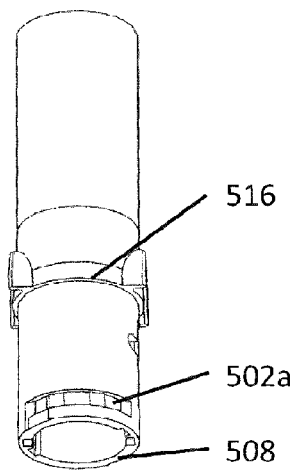
FIG. 23 shows a perspective view of the case of FIG. 20 from below.

The tubular wall 501b may have an inner diameter D52, as shown in FIG. 24, ranging for example from 6.5 mm to 24.5 mm, e.g. 13.0 mm. The inner diameter D52 corresponds to the outer diameter D35 of the reservoir 3 (FIG. 8), taking into account a small spacing, e.g. less than 0.2 mm to allow easy, e.g. substantially friction-less displacement of the reservoir 3 with respect to the case 5, and to take into account any production tolerances (that is to say: the friction between the outer surface of the reservoir 3 is preferably substantially friction-less with respect to the inner surface of the case 5. The friction/resistance caused by the snaps 510 in contact with the pens 308, as discussed above, is a different matter). The case 5 may have one or more delimiting walls separating the first and the second segments 501a, 501b from one another, e.g. one delimiting wall 507, located at distance L54, as shown in FIG. 24, from the surface 508 (FIG. 23). This distance L54 may range for example from 15.0 mm to 45.0 mm, e.g. 28.0 mm, and should be larger than the length L31 of the reservoir 3 (FIG. 8).

One or more second grooves, e.g. two grooves 509a, 509b, may be provided in the wall 501b. They may be substantially parallel to the longitudinal axis of the case 5. The width W51, as shown in FIG. 29, of these grooves 509a, 509b corresponds to the dimensions of the pens 308a, 308b (FIG. 8), taking into account a small spacing, e.g. 0.2 mm to allow easy displacement of these pens 308a, 308b in the second grooves 509a, 509b, and to take into account any production tolerances (that is, without taking into account the deliberate friction/resistance caused by the snaps 510 upon the pens 308). One or more snaps, e.g. two snaps 510a, 510b, may be provided inside the second grooves 509a, 509b. The snaps may take the form of a longitudinal part that can bend in radial direction, towards the longitudinal axis of the case 5. But other snaps are also possible, e.g. by varying the depth of the longitudinal groove 509. These snaps 510a, 510b have a double function; providing a deliberate friction/resistance/counter pressure to the reservoir 3 to prevent the reservoir 3 to move unintentionally (e.g. due to gravity or inertial forces due to sudden movements of the device 9), and providing the possibility to function as a permanent lock after the device 9 has been used, as will be explained further with respect to the top ends 518 and the open end 519.

One or more third grooves, e.g. two circumferential grooves 511a, 511b (FIG. 29), may be provided perpendicular to the second grooves 509a, 509b. They are connected and form a T-shaped perforation in the lower part of the case 501b. The grooves 511a, 511b provide a space for holding the pens 308a, 308b after assembly, but before activation of the device 9. The grooves 511 may have a length L55, as shown in FIG. 29, ranging for example from 1.0 mm to 8.0 mm, such as less than 3.5 mm, e.g. 2.5 mm, so as to limit the rotation angle needed to unlock the device 9. The third grooves 511a, 511b may have a height H52, as shown in FIG. 29, corresponding to the dimensions of the pens 308a, 308b, taking into account a limited spacing, e.g. 0.2 mm to allow easy displacement of these pens 308a, 308b in the third grooves 511a, 511b, and to take into account any production tolerances. The snaps 510a, 510b might be bent inwards so as to provide sufficient counter pressure to the reservoir 3 and to block the exit of the third grooves 511a, 511b. Above the snaps 510a, 510b a sufficiently large expansion might be left in the second grooves 509a, 509b to provide space for receiving and permanently holding the pens 308a, 308b after administration of the fluid and release of the plunger 6 (as will be described further). The snaps 510a, 510b may have a circular cut on the top end 518 so as to provide a large contact surface with the pens 308a, 308b after locking of the device 9, i.e. when the pens 308 are moved into the open ends 519. One or more fourth grooves, e.g. two grooves 512a, 512b (FIG. 28) (512a not shown), may be provided, parallel to the second grooves 509a, 509b, in the wall 501b. These fourth grooves 512a, 512b provide a way through which the pens 308a, 308b can be shifted during assembly to their starting position in the third grooves 511a, 511b. The fourth grooves 512a, 512b may have an inclination, to facilitate the assembly of the reservoir 3 in the case 5. The dimensions of the second grooves 509a, 509b, the snaps 510a, 510b, the third grooves 511a, 511b and the fourth grooves 512a, 512b may depend on the dimensions of other parts, e.g. the needle 7 and the reservoir 3.

Relation Between the Case 5 (Fifth Part), the Plunger 6 (Sixth Part) and the Spring 8 (Eighth Part)

Figure 38:
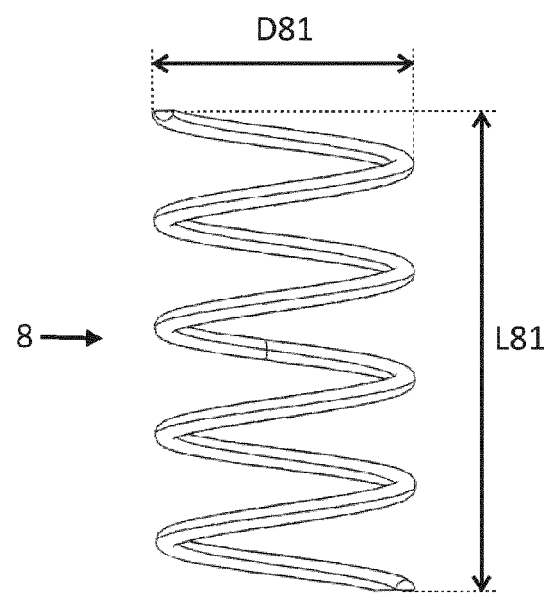
FIG. 38 shows a front view of an embodiment of the spring (eighth part) of the device according to embodiments of the present invention.
Figure 39:
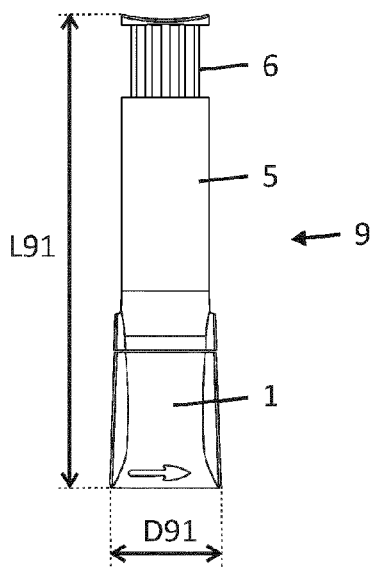
FIG. 39 shows a front view of an embodiment of the assembled device according to embodiments of the present invention.

One or more delimiting walls, e.g. one delimiting wall 507, may be provided inside the case 5 at a distance L56, as shown in FIG. 24, from the end surface 513 of the case 5, ranging for example between 3.0 mm and 30.0 mm, such as between 15.0 mm and 25.0 mm, e.g. 20.0 mm, to ensure the total length L91 of the assembled device 9 is as ergonomically fitting in a human's hand as possible. This length L56 corresponds to the length L81 of the spring 8 (FIG. 38). A first opening, e.g. a circular opening 514 (FIG. 26), may be provided in the delimiting wall 507. In case the first opening 514 has a circular shape, it may have a diameter D53, as shown in FIG. 24, ranging for example between 3.0 mm and 20.0 mm, such as between 3.0 mm and 10.0 mm, e.g. 6.5 mm, to obtain a total diameter D92 of the assembled device 9 that can be firmly held in a human hand. The diameter D53 corresponds to the diameter D63 (FIG. 34) of the plunger 6, taking into account a small spacing, e.g. less than 0.2 mm, to allow easy displacement of the plunger 6 during assembly, penetration of the skin, administering fluid e.g. drugs and de-activation of the device 9, and to take into account any production tolerances. Adjacent to the first opening 514 one or more second openings, e.g. two second openings 515a, 515b (FIG. 26) may be provided. These second openings 515a, 515b may have a width W52, as shown in FIG. 27, ranging for example between 0.5 mm and 5.0 mm, e.g. 2.0 mm. This width W52 corresponds to the width W62 (FIG. 34) of the plunger 6, taking into account a small spacing, e.g. less than 0.2 mm, to allow easy displacement of the plunger 6, and to take into account any production tolerances. The second openings 515a, 515b ensure the plunger 6 cannot rotate inside the case 5. The purpose hereof is to make sure that the plunger 6 is deliberately misaligned to grooves 314 of the reservoir 3 after assembly (in locked mode of the device 9), and is deliberately aligned to the grooves 314 of the reservoir in the activated mode of the device 9, after rotation of the foot 1.

The Plunger 6, Also Referred to as the Sixth Part

Figure 32:
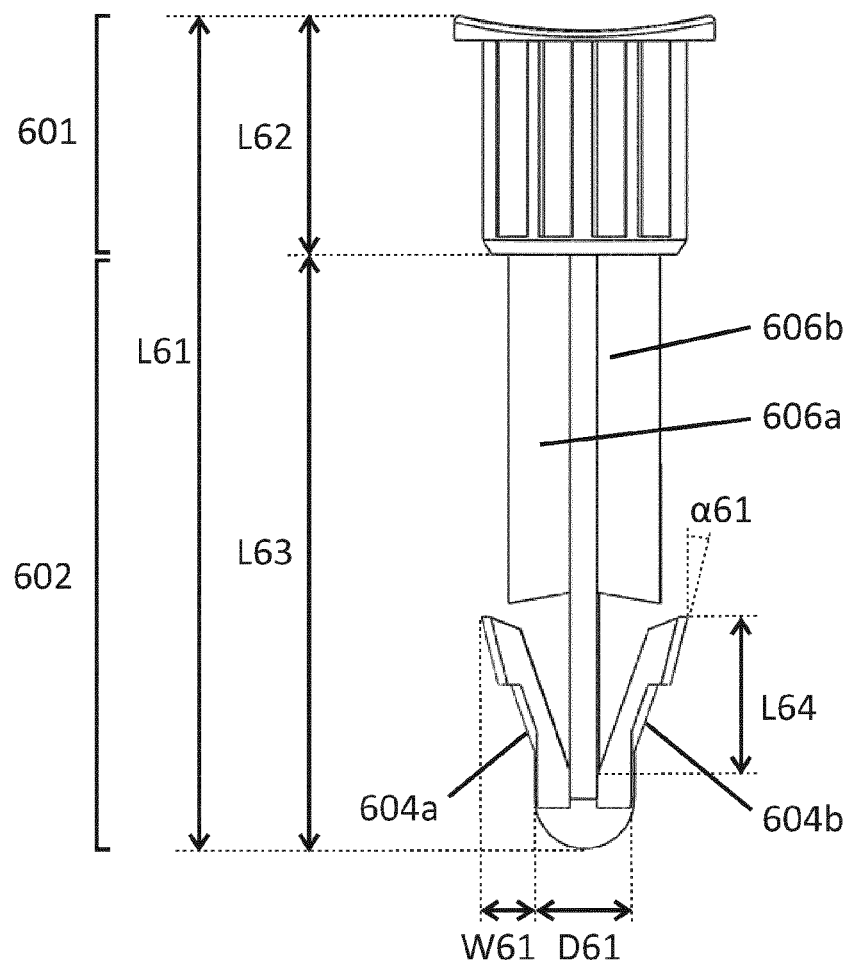
FIG. 32 shows a front view of an embodiment of the plunger (sixth part) of the device according to embodiments of the present invention.

The plunger 6, also referred to as the sixth part, will be explained with reference to FIGS. 32-34. The plunger 6 is an elongated part comprising a main body 601 and a secondary body 602 and having a total length L61, as shown in FIG. 32, ranging between 25.0 mm and 60.0 mm, e.g. 43.0 mm. The main body 601 may have a tubular shape, e.g. a cylindrical shape to gradually increase friction as the plunger 6 glides into the case 5. Parts of the main body 601 may be left out, as shown in FIG. 32 (where a cylindrical shape has been cut down, and only central ribs remain), so as to avoid the main body of the plunger 6 to be a solid volume and to ensure a substantially constant wall thickness across the whole part, that can be moulded. The main body 601 has a first end with a surface, e.g. a concave top surface 607, adapted to provide an ergonomic support for finger placement. The secondary body 602 may exhibit rotational symmetries, so as to distribute forces and ensure stability.

Relation Between the Plunger 6 (Sixth Part), the Reservoir 3 (Third Part) and the Seal 4 (Fourth Part)

The secondary part 602 of the plunger has a head 603 at the opposite end of the surface 607. The head 603 may have a rounded shape, e.g. a dome or semi-spherical shape. This shape corresponds to the form of the lower surface of the hollow space 312 for containing the fluid, e.g. drugs, in the reservoir 3. In case the head 603 takes the form of a semi-sphere it has a diameter D61, as shown in FIG. 32, ranging for example between 1.8 mm and 7.8 mm, such as between 2.8 mm and 3.8 mm, e.g. 3.3 mm so as to keep the length L91 and diameter D92 ratio of the assembled device 9 as ergonomic as possible. The diameter D61 of the plunger head 603 corresponds to the diameter D36 of the hollow space 312 and the thickness T41, taking into account a small spacing, e.g. less than 0.2 mm, to allow an easy displacement of the plunger head 603 into the space 312 of the reservoir 3, while the small spacing can be filled when the end portion 402 of the seal 4 is to be clamped between the dividing wall 311 of the reservoir 3 and the plunger head 603, and to take into account production tolerances. On the secondary plunger body 602, one or more snaps, e.g. two snaps 604a, 604b, may be provided to prevent the plunger head 603 to exert pressure before the device 9 is activated, on the central body of the seal 402 and hence on the hollow space 312 in the reservoir 3 containing the fluid, e.g. drug. These snaps 604a, 604b have a length L64, as shown in FIG. 34, ranging for example between 4.0 mm and 15.0 mm, e.g. 7.5 mm. The snaps 604a, 604b have a width W61, as shown in FIG. 32, ranging between 1.0 mm and 10.0 mm, for example less than 5.0 mm, e.g. 3.0 mm, so as to keep the total diameter D92 of the assembled device 9 to a thickness that is ergonomic. Each snap 604a, 604b has a snap head 605a, 605b. The form and dimensions of these snap heads 605a, 605b may correspond to the form and dimensions of the grooves 314a, 314b and the openings 313a, 313b, taking into account a small spacing, e.g. 0.2 mm so as to allow displacement of the snap heads 605a, 605b into the grooves 314a, 314b and the openings 313a, 313b of the reservoir 3

Figure 55:
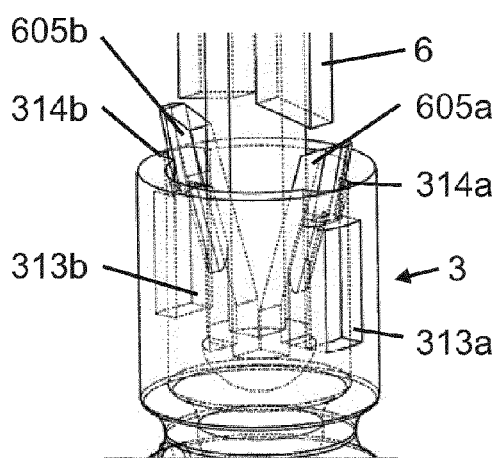
FIG. 55 shows a perspective view of the relative position of the plunger and the reservoir after the device is unlocked but before the plunger is pressed.
Figure 56:
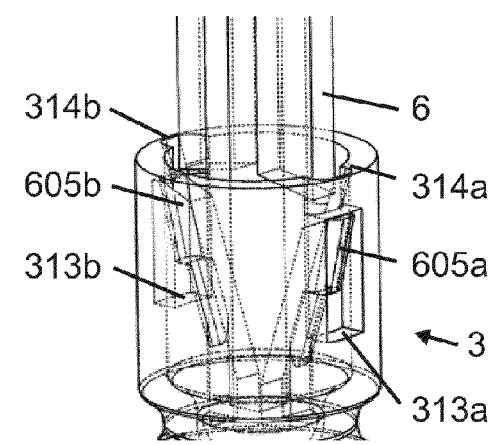
FIG. 56 shows a perspective view of the relative position of the plunger and the reservoir after the plunger is pressed and the liquid is removed from the device.

(see FIGS. 55 and 56). The snap heads 605a, 605b may have a width W62, as shown in FIG. 34, ranging between 0.8 mm and 5.8 mm, e.g. 1.6 mm. This width W62 may correspond to the width W32 of the grooves 314a, 314b, taking into account a small spacing, e.g. less than 0.2 mm to allow easy displacement of the plunger 6, and to take into account production tolerances. The snap heads 605a, 605b may have an inclination with an angle α61 with respect to the longitudinal direction of the plunger, as shown in FIG. 32, ranging for example between 0.0° and 50.0° and corresponding to the angle α33, such as for example between 20.0° and 40.0°, e.g. 30.0° to ensure that, after penetration of the skin and before administration of the fluid, e.g. drug, a force applied to the top surface 607 and directed towards the plunger 603, and having a sufficient magnitude, e.g. at least 1 Newton, causes the snap heads 605a, 605b to slide through the grooves 314a, 314b into the openings 313a, 313b. The angle α61 and/or the width W62 and/or the force constants of 604a, 604b acting as wires and/or surface finishing of the snap heads 605a, 605b are chosen to ensure that the friction between the reservoir 3 and the plunger 6 is larger than the sum of the friction between the reservoir 3 and the case 5 and the friction for the needle 7 to penetrate the skin, so as to ensure that the skin is penetrated only after the fluid in the hollow space 312 is squeezed out, but not as large to prevent the operator to displace the plunger 6 in the reservoir 3 altogether. The corners of the snap heads 605a, 605b may be rounded so as to avoid stress concentration points while positioned inside the grooves 314a, 314b.

Relation Between the Plunger 6 (Sixth Part) and the Case 5 (Fifth Part)

The main body 601 of the plunger 6 has a length L62, as shown in FIG. 32, ranging for example between 4.0 mm and 30.0 mm, e.g. 13.0 mm. The secondary body 602 of the plunger 6 has a length L63, as shown in FIG. 32, ranging for example between 15.0 mm and 60.0 mm, e.g. 31.0 mm. The length L62, L63 of the first resp. second plunger body 601, 602 corresponds to the dimensions of the other parts, e.g. the case 5, resp. the reservoir 3. In case the main plunger body 601 has a cylindrical shape, it may have a diameter D62, as shown in FIG. 34, ranging for example between 6.3 mm and 24.3 mm, e.g. 12.8 mm. The diameter D62 corresponds to the inner diameter D52 of the tubular wall 501a, taking into account a small spacing, e.g. less than 0.2 mm so as to allow an easy displacement of the plunger 6 in the case 5, and to take into account any production tolerances. The secondary plunger body 602 may be delimited by a cylindrical shape with a diameter D63, as shown in FIG. 34, ranging for example between 2.8 mm and 19.8 mm, such as between 2.8 mm and 9.8 mm, e.g. 6.3 mm. These dimensions are chosen such that the total diameter D92 of the assembled device 9 is limited to an ergonomically acceptable value. The diameter D63 (FIG. 34) of the secondary plunger body 602 corresponds to the inner diameter D53 of the delimiting wall 507 (FIG. 24), taking into account a small spacing, e.g. less than 0.2 mm so as to allow an easy displacement of the plunger 6 in the case 5, and to take into account production tolerances. One or more ribs, e.g. two ribs 606a, 606b (FIG. 32), may be provided on the secondary body 602. These ribs 606a, 606b correspond in shape to the openings 515a, 515b (FIG. 27) in the delimiting wall 507 of the case 5 and may have a width W63, as shown in FIG. 34, ranging for example between 0.3 mm and 4.8 mm, e.g. 1.8 mm. This width W63 corresponds to the width W52 (FIG. 27) of the second openings 515, taking into account a small spacing, e.g. less than 0.2 mm, to allow easy displacement of the plunger 6, and to take into account any production tolerances. The ribs 606a, 606b and the second openings 515 ensure the plunger 6 cannot rotate inside the case 5. As mentioned above, the purpose hereof is to make sure that the plunger 6 is deliberately misaligned to grooves 314 of the reservoir 3 in locked mode of the device 9, and is deliberately aligned to the grooves 314 of the reservoir in the activated mode of the device 9.

The Needle 7, Also Referred to as the Seventh Part

Figure 35:
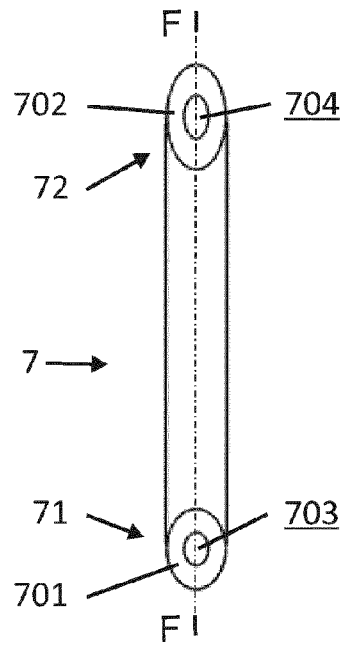
FIG. 35 shows a front view of an embodiment of the needle (seventh part) of the device according to embodiments of the present invention.

The needle 7, also referred to as the seventh part, will be explained with reference to FIGS. 35-37. The needle 7 is a hollow tubular part, for example substantially cylindrical, with outer diameter denoted D71 and an inner diameter denoted D72, with two open ends, a first end 71 for penetrating a subject's skin, the first end 71 having a first opening 703 for injecting fluid, e.g. drug, and a second end 72 for penetrating the wall section 316 of the reservoir 3, the second end having a second opening 704 for accepting the liquid from the reservoir 3.

Figure 36:
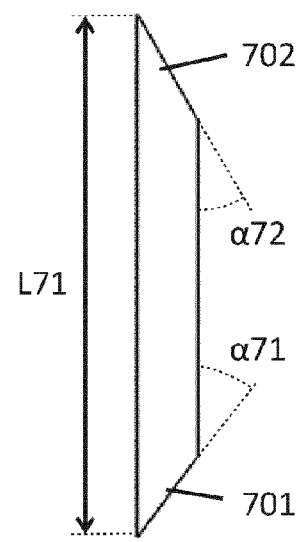
FIG. 36 shows a side view of the needle of FIG. 35.
Figure 37:
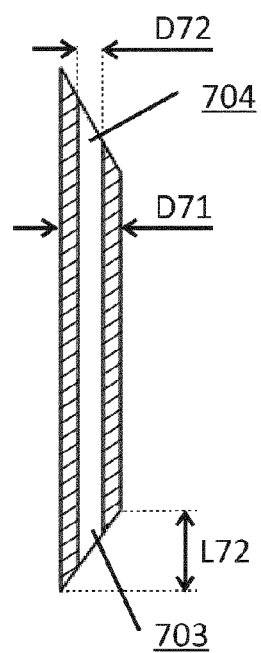
FIG. 37 shows a front view of the cross section of the needle of FIG. 35 when cut by plane F-F.

The needle 7 has a length L71, as shown in FIG. 36, ranging for example between 5.0 mm and 30.0 mm, e.g. about 15.0 mm. This length corresponds to various dimensions of other parts and function of the device, e.g. the foot 1 and the needle hub 2 and penetration depth L. The dimensions of the needle 7 and dimensions of other parts of the device 9 are such that the needle 7 can penetrate the skin and ensures administering the fluid in the hollow space 312 without leakages in a controlled zone of controlled depth of mammalian skin, where the only major limiting factor is viscosity of the substance. The length of the zone corresponds to the height of the first opening L72 along the longitudinal axis of the needle 7, indicated in FIG. 37, may be smaller than or equal to the intradermal layer at preferred locations such as the forearm or upperarm (deltoid), e.g. the zone in which administration occurs, may range from 0.5 mm to 1.75 mm beneath the outer surface of the dermis. The needle is neither visible nor reachable before and after administration and neither visible nor reachable when administration occurs. This helps to prevent needle stick accidents, and reduces the risk for contamination.

The needle 7 may have a first bevel 701 on the first end 71 of the needle 7, adapted for penetrating the subject's skin. The surface of the first end 71 of the needle 7 may be substantially located in a first plane. The first plane has an angle α71 with regard to the longitudinal axis of the needle 7, as indicated in FIG. 36, ranging from 20.0° to 60.0°, e.g. 35.0°, so as to be sharp enough to penetrate the skin 91 with minimum deformation of the first needle end 71, and so that only a very small force (e.g. less than 5 Newton, preferably less than 3 Newton) is required to insert the needle end 71 into the skin.

In case the surface of the first end 71 of the needle 7 is substantially located in a plane, one factor for controlling the zone at which fluid, e.g. drug, is administered, is α71, for the length L72 is substantially determined by the identity $L72 = D71/\sin(\alpha 71)$; the larger L72, the less precise the depth position of the needle opening 703 in the subject's skin will be; however, the less pressure will be exerted by penetrating the skin, the less pain the subject will perceive. As the penetration depth for intradermal injections is very important for the efficiency of the drug, the penetration depth needs to be within small limits. One of the aspects to reach these limits is the angle α71.

The needle 7 may have a second bevel 702 on the second end 72 of the needle 7, adapted for penetrating the reservoir 3, more particularly for penetrating the wall section 316 (FIG. 15). The surface of the second end 72 of the needle 7 may be substantially located in a second plane. The second plane has an angle α72 with regard to the longitudinal axis of the needle, as indicated in FIG. 36, for example ranging between 20.0° and 40.0°, for facilitating penetration of the second needle end 72 into the wall section 316 of the reservoir 3. An angle α72 of the second bevel 702 larger than 20.0° limits the size of the second needle opening 704. Limiting the size of the second opening 704 may result in a smaller length L91 of the assembled device 9. The angle α72 should be sufficiently large for avoiding bending or breaking of the second needle end 72 when penetrating the wall section 316 of the reservoir 3. For given materials of the needle 7 and the reservoir 3, the skilled person can find suitable angles by doing routine tests. However the surface of the second end 72 need not necessarily be located in a plane.

As the assembled device 9 is primarily aimed at intradermal injections, suitable needles may have for example an outer diameter D71 ranging from 0.1842 mm (34 G) to 0.4636 mm (26 G) and a (strictly smaller) inner diameter D72 ranging from 0.0826 mm (34 G) to 0.260 mm (26 G). As an example only, an outer diameter of 0.2096 mm (33 G) and an inner diameter of 0.108 mm may be used. An inner diameter of 0.826 mm (34 G) or smaller may not allow a sufficiently large flow rate under moderate pressure, thus preventing a liquid, e.g. a drug, to pass through the needle fast enough. Assuming a constant injection pressure, a smaller inner diameter results in a slower injection and may cause more pain to the subject. In case an inner diameter from 0.108 mm to 0.260 mm, the flow rate will be sufficiently large, but a larger inner diameter D72 results in a larger outer diameter D71 of the needle 7 and a smaller α71 to control the administration zone, which may cause a more intense pain sensation to the subject when penetrating the skin.

The needle 7 may be constructed of one or more of a variety of materials, e.g. metal, metal alloys, polymers, ceramics or biodegradable materials. The needle 7 is assembled in the needle hub 2 in opening 206 (FIG. 7). It is firmly held into position, e.g. by glue, fillers or by tension between needle 7 and needle hub 2.

The Spring 8, Also Referred to as the Eighth Part

The spring 8, also referred to as the eighth part, will be explained with reference to FIG. 38. The spring 8 may be any suitable type of spring, e.g. a helical compression spring or a barrel spring. It may have one or more wires, e.g. a double wire spring. In case a helical compression spring is used for the eighth part, it may have an outer diameter D81, as shown in FIG. 38, ranging for example between 5.0 mm and 15.0 mm, e.g. 10.0 mm. This diameter D81 corresponds to the dimensions of other parts, e.g. the plunger 6 and the case 5. The spring 8 has a free length L81, as shown in FIG. 38, ranging for example between 5.0 mm and 40.0 mm, such as less than 20.0 mm, e.g. 18.0 mm, to limit the total length L91 of the assembled device 9. This free length L81 may correspond to the dimensions of other parts, e.g. the case 5 and the reservoir 3, as configured in the initial position of the device 9.

The spring 8 should have a sufficient stiffness (force constant) to be able to exert a force sufficiently large to push back the plunger 6, when released by the user after administration of the fluid, and along with the plunger 6 also the reservoir 3 attached thereto by the snap heads 605a, 605b of the plunger 6 being trapped in the openings 313a, 313b of the reservoir 3, in the longitudinal direction (away from the skin). During this motion, the pens 308a, 308b of the reservoir 3 slide through the second grooves 509 and are in sliding contact with the snaps 510a, 510b of the case 5.

The spring force should be sufficiently large to pull the needle 7 back from the skin, and to overcome the friction/resistance between the snaps 510 and the pens 308. When moving upwards (away from the skin), the pens 308 move past the third grooves 511, and continue to move until the pens 308 arrive at the (upper) end of the grooves 509, where an opening is provided for receiving the pens 308. When the pens 308 are in this opening, top ends of the snaps 510 are moved inwards for permanently blocking the position of the pens 308, thereby blocking the position of the reservoir 3 (and the needle hub 2 and the needle 7) with respect to the case 5. The spring 8 may be compressed at initial position of the device 9 (locked mode).

However, the stiffness of the spring 8 should not be so large that it cannot be compressed with a reasonable force during use of the device 9. During administration of the fluid, the force exerted upon the plunger top surface 607 should be sufficiently large for inserting the first needle end 71 in the subject's skin and, subsequently, inducing a sufficient amount of pressure on the seal 4 to administer the fluid in a time span that is maximally comfortable for subject and operator, e.g. between 0.1 and 10.0 seconds, for example about 3.0 seconds. The spring stiffness may be such that the force to be exerted on the plunger top 607 against the force exerted by the compressed spring and to overcome the first and/or second friction mentioned above, lies between 0.5 N and 40.0 N, for example between 1.0 N and 20.0 N, such as between 2.0 N and 10.0 N, e.g. is about 4.0 N. The skilled person can design a suitable spring 8 using standard design techniques and routine test methods that satisfies this requirement, e.g. a spring 8 with a force constant of k=1.12 N/m, taking account of all other given dimensions of the device.

A wired spring may comprise or consist of stainless steel, but can also comprise or consist of other suitable materials such as e.g. a polymer. The spring stiffness may be conserved during preliminary processes such as sterilization, e.g. by exposure to gamma radiation.

Detailed Description of the Assembly of the Device 9

The assembly of the device 9 will be described with reference to FIGS. 1-40. The assembly process described below is only one possible example. Alternative assembly methods are equally possible, in particular, the order of assembling the parts 1 to 8 may be modified.

Materials

Foot 1, needle hub 2, reservoir 3, case 5 and plunger 6 may be manufactured from any suitable material, such as biodegradable materials or polymers, e.g. medical grade polypropylene. Seal 4 may be produced from a flexible or elastic material, e.g. a vulcanized thermoplastic. Spring 8 may be made from any suitable material; it may for example comprise or consist of a metal, a metal alloy, or a polymer. The needle 7 may be constructed of one or more of a variety of materials, e.g. metal, metal alloys, polymers, ceramics or biodegradable materials.

Assembly should preferably take place in a clean environment, such as e.g. in a clean room facility.

Assembly Step 1: Reservoir 3 and Seal 4

In a first step, the seal 4 may be forced into reservoir 3, while air can escape through openings 313a and 313b and other grooves. Corresponding diameters D34 and D41 may ensure a rigid clamping of both parts 4, 3. When the surface 401 mates hollow space 312, the seal 4 is located in the correct position.

Assembly Step 2: Filling of the Reservoir 3

There are different ways to fill the space 312 of the reservoir 3 with a liquid, e.g. with a drug or vaccine. The space 312 can be filled before assembling the seal 4.

Alternatively, the seal 4 is first installed halfway space 312. The reservoir 3 can then be tilted, and space 312 can then be filled, e.g. via a needle applied through one of the openings 313a or 313b, such that the needle tip is located below the seal 4. After the amount of liquid is injected into the space 312, the seal 4 is pushed into its final position for closing the hollow space 312.

Alternatively the seal 4 is first installed in its final position for closing the hollow space 312, and then a liquid is introduced in the space 312 by means of a sharp device 9, e.g. a needle inserted through the seal 4. Air can escape through the filling device, or through an additional device (for example a second needle inserted through the seal 4). The elastic characteristics of the seal 4 can prevent the reservoir 3 from leaking after the sharp filling device is removed.

Alternatively, any other manual or automated method can be used to fill the space 312 of the reservoir 3.

Assembly Step 3: Needle 7 and Needle Hub 2

The needle 7 may be mounted in needle hub 2 in any suitable way, e.g. by tension, welding, moulding, glue or a filler. The needle 7 may be placed and fixed in channel 206 in a calibrated position.

Assembly Step 4: Needle Hub 2 and Reservoir 3

The needle hub 2 with needle 7 attached to it may then be snapped in reservoir 3. Alternatively, the needle hub 2 may first be snapped in the reservoir 3, and the needle 7 may be attached thereto only later. Pens 203a and 203b of the needle hub 2 can slide into grooves 307a and 307b of the reservoir 3, before arriving into the bottom part of grooves 305a and 305b (FIG. 11). The outer surface 201 of the needle hub 2 may be guided by the wall of the second segment 302 of the reservoir with inner diameter D31 (FIG. 12).

Assembly Step 5: Reservoir 3 and Case 5

The reservoir 3 may then be mounted in case 5 by sliding the pens 308a and 308b of the reservoir 3 (FIG. 14) through the grooves 512a and 512b of the case 5 (FIG. 28), until they snap into the third grooves 511a and 511b of the case 5. The outer surface of reservoir 3 with diameter D35 (FIG. 8) may be guided by the inner surface of the case 5 with diameter D52 (FIGS. 12 and 14).

Assembly Step 6: Foot 1 and Case 5

The foot 1 may be snapped in case 5 by guiding the pens 103 (FIG. 3, FIG. 4) through the insertion portions 506a and 506b (FIG. 22 and FIG. 30), and forcing the pens 103 into the circumferential grooves 502. The inner surface of the foot 1 with diameter D12 (FIG. 3) may be guided by the outer surface of the case 5 with diameter D51 (FIG. 21).

Assembly Step 7: Plunger 6 and Spring 8

The spring 8 may be forced over snap heads 605a and 605b of the plunger 6 (FIG. 32). The spring 8 may be centred with respect to the secondary body 602 of the plunger 6.

Assembly Step 8: Plunger 6 and Case 5

Figure 26:
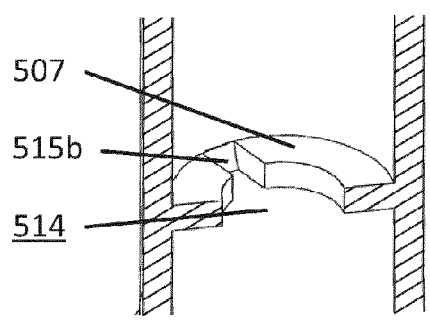
FIG. 26 shows a perspective view of a close-up of the case of FIG. 24.
Figure 27:
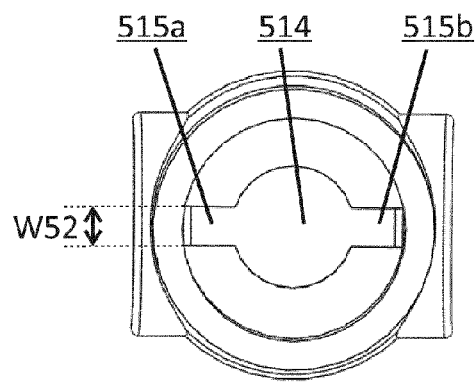
FIG. 27 shows a top view of the case of FIG. 20.

Plunger 6 (FIG. 32) may be guided by inserting its ribs 606a and 606b into the second openings 515a and 515b in the delimiting wall 507 of the case 5 (FIG. 26). When mounting depth is sufficient, snap heads 605a and 605b of the plunger 6 may snap behind the straight edge (90° angle) of slots 515a and 515b (as may be seen in FIG. 26 and FIG. 27). At this point, spring 8 will be slightly compressed between the surface 507 of the case 5 and the surface 608 of the plunger 6.

At this point, the device 9 is ready for packing, sterilization and application (see mode of action). Instead of sterilizing the assembled device 9 after assembly, it is also possible to sterilize the individual parts 1-8 of the device 9 beforehand, e.g. in a clean room, and to fill the reservoir 312 with the vaccine, and to assemble the device 9 also in the clean room.

Detailed Description of the Mode of Action of the Device 9

The mode of action of the device 9 will be described with reference to FIGS. 41-54 and will be explained in several steps.

Figure 41:
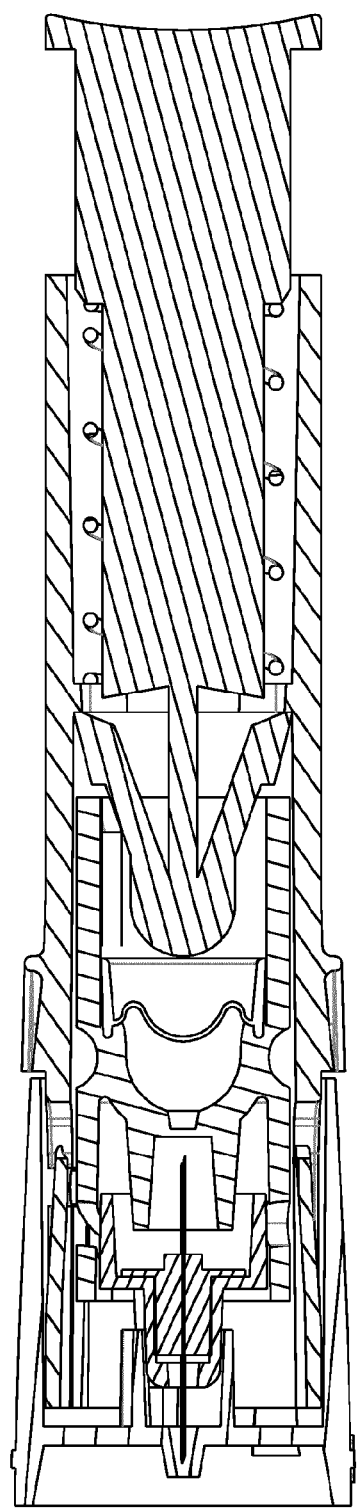
FIG. 41 shows the relative position of the parts of the device in the first mode, this means before the device is unlocked.
Figure 42:
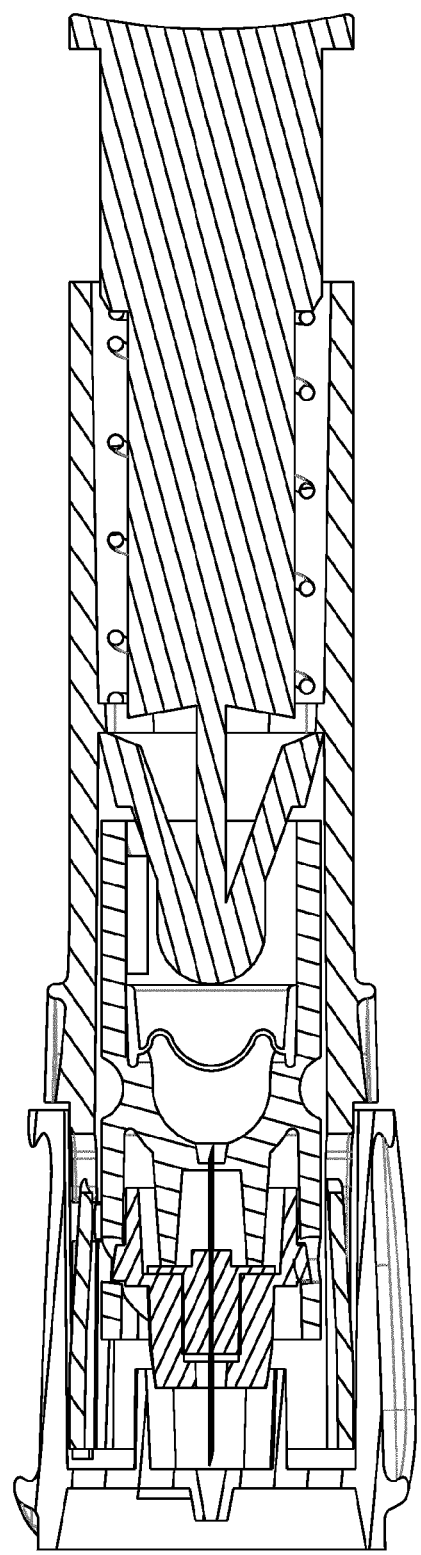
FIG. 42 shows the relative position of the parts of the device in the second mode, this means after the device is unlocked.
Figure 43:
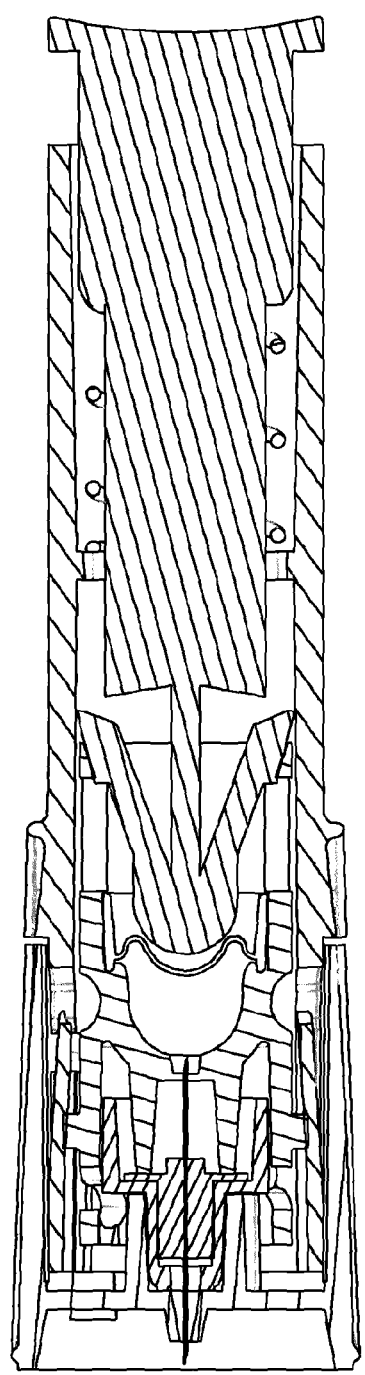
FIG. 43 shows the relative position of the parts in the second mode, when the plunger is halfway moved towards the foot.
Figure 44:
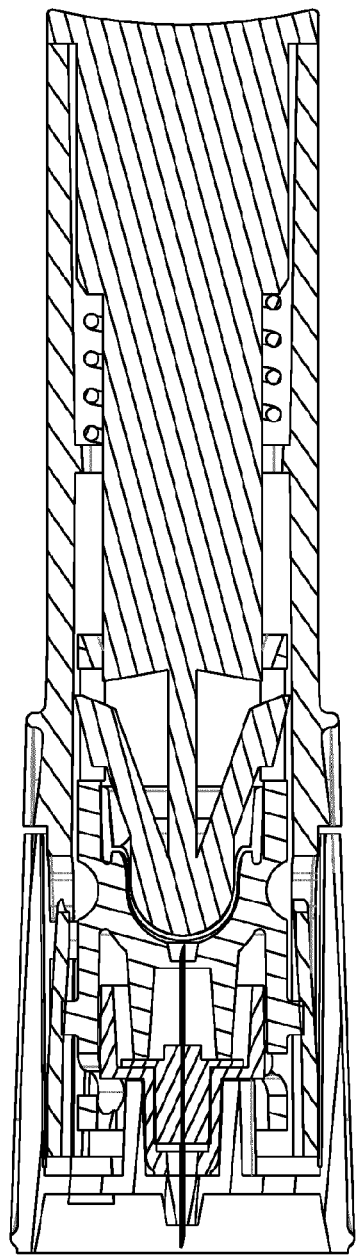
FIG. 44 shows the relative position of the parts of the device in the second mode, when the plunger has moved completely towards the foot.
Figure 45:
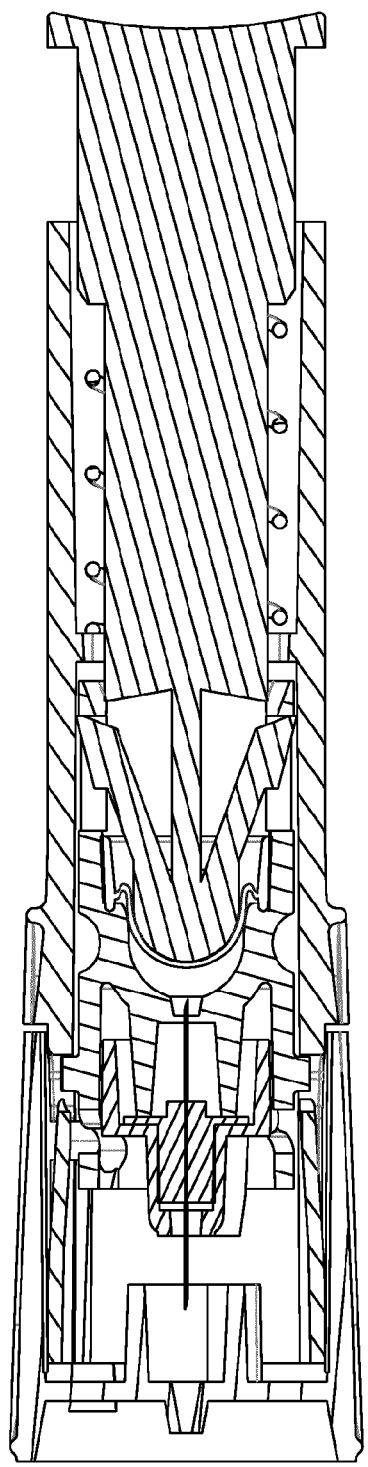
FIG. 45 shows the relative position of the parts of the device in the third mode, this means after the device is safety locked.

In use of the device 9, three steps can be distinguished. The position of the parts 1-8 of the device 9 before the first step, but after assembly, are shown in FIG. 41, and will be described in detail below. The first step is the "unlocking" of the device 9. The relative position of the parts 1-8 after unlocking the device 9 is shown in FIG. 42. The second step is the "pressing of the plunger 6". The relative position of the parts 1-8 after the plunger 6 is pressed so as to move approximately halfway is shown in FIG. 43, and after the plunger 6 is pressed so as to move completely is shown in FIG. 44. The third and last step is the "automatic safety positioning" after the injection is applied to the subject, and is entered automatically when the plunger 6 is released. The relative position of the parts 1-8 after the third step is shown in FIG. 45.

Figure 46:
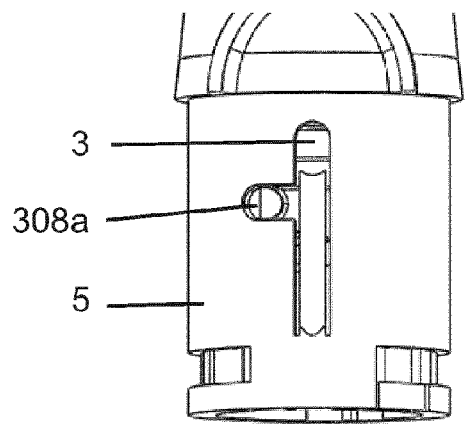
FIG. 46 shows a perspective view of the relative position of the case and the reservoir before the device is unlocked.
Figure 47:
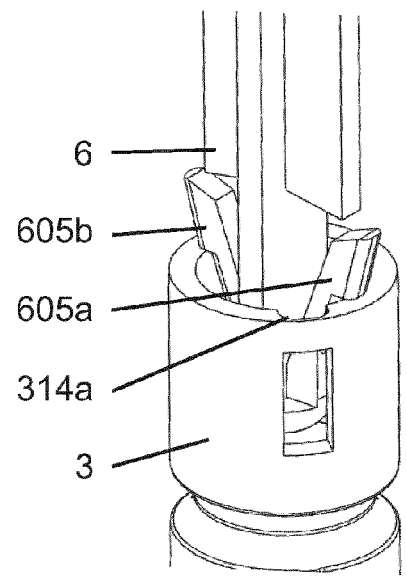
FIG. 47 shows a perspective view of the relative position of the plunger and the reservoir before the device is unlocked.

In the first state (also called "locked mode") of the device 9, which is the mode the device 9 is in after assembly, as shown in FIG. 41, the internal components, e.g. the plunger 6 and the reservoir 3, cannot accidentally be pressed downwards. With "downward" movement is meant a movement from the plunger 6 towards the opening 102 in longitudinal direction of the device 9. A downward movement of the reservoir 3 is prevented since the pens 308a, 308b of the reservoir 3 are still positioned inside the circumferential part of the third grooves 511a, 511b, as shown in FIG. 46. In addition, the snap heads 605a, 605b of the plunger 6 are not yet aligned above the grooves 314a, 314b of the reservoir 3, as shown in FIG. 47, thus preventing the plunger 6 to be pushed downwards. Since the needle 7 and the needle hub 2 are connected to the reservoir 3 (albeit rotationally movable, FIG. 49), the needle 7 cannot move up or down either by pressure exerted upon the plunger 6. This ensures that the needle 7 does not extend through the opening 102, and cannot exit the device 9 before the device 9 is deliberately unlocked. In the "locked mode" the spring 8 is in its least compressed state.

First Step: Rotation of the Foot, Unlocking the Device 9

Figure 48:
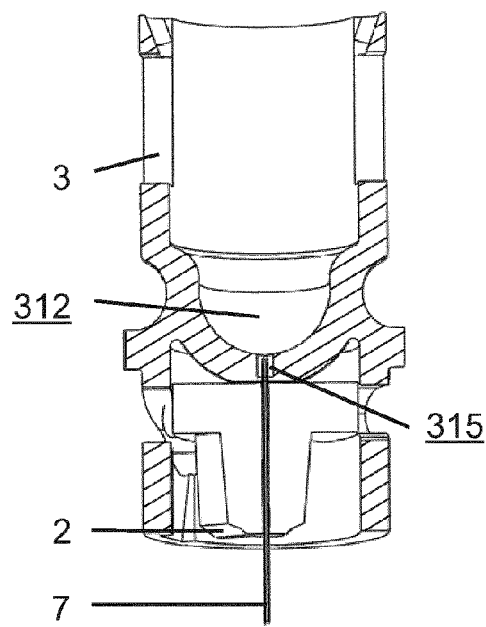
FIG. 48 shows a cross section of the relative position of the needle hub, the needle and the reservoir after the device is unlocked but before the plunger is pressed.
Figure 49:
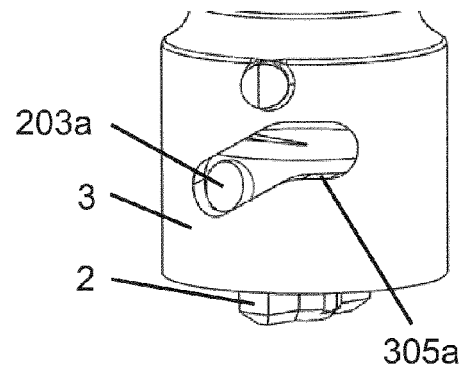
FIG. 49 shows a perspective view of the relative position of the needle hub and the reservoir before the device is unlocked.

A first step comprises the unlocking of the device 9 (FIG. 49). A user unlocks the device 9 by rotating the foot 1 of the device 9 over a predefined angle, with respect to the longitudinal axis of the device 9. This angle is determined by the dimensions of the circumferential groove 502 (FIG. 30 in the embodiment shown in FIG. 49, the foot first needs to be rotated over an angle of about 50° until the pen 203 reaches an end position in the groove 305, and then needs to be rotated further over about 25° in clockwise direction until the pen 308 has moved inside the second grooves 509 (FIG. 46), but other angles such as e.g. any angle from 10.0° to 90.0° may also be used. In an alternative embodiment (not shown), where the third groove 511 would be located on the other side of the second groove 509 (on the left side thereof, in FIG. 28), the direction of rotation to unlock the device 9 would be counter-clockwise. The rotation of the foot 1 is typically done in a single smooth movement, but will be described in several small steps. The wall 108 of the foot 1 (FIG. 4) and the bulge 202 (FIG. 5) of the needle hub 2 create a connection between the foot 1 and the needle hub 2, and ensure the needle hub 2 rotates along with the foot 1 when being rotated. The pens 203a, 203b (FIG. 5, FIG. 49) of the needle hub 2 slide through the grooves 305a, 305b of the reservoir 3 (FIG. 11, FIG. 49). The shape of the grooves 305a, 305b ensures the pens 203a, 203b of the needle hub 2, and thus the entire needle hub 2, moves upwards (i.e. towards the plunger 6). Since the needle 7 is attached to the needle hub 2 it is also pushed upwards, and the second end 72 of the needle 7 with the bevel 702 penetrates the bottom wall section 316 of the reservoir 3 (FIG. 15, FIG. 48). When the upper part of the second end 72 of the needle 7 with the bevel 702 has entered into the cavity 315, liquid inside the actual reservoir 3, i.e. the space 312, can penetrate the needle 7. It is noted however, that since the needle tip is inserted from the bottom, no pressure is exerted upon the fluid at this stage, thus only a minimal amount of fluid will escape from the reservoir, if any.

Figure 50:
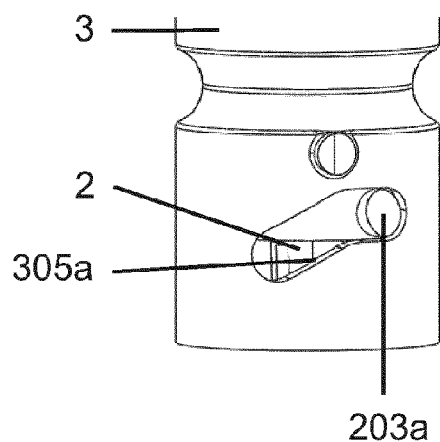
FIG. 50 shows a perspective view of the relative position of the needle hub and the reservoir after the device is unlocked.
Figure 51:
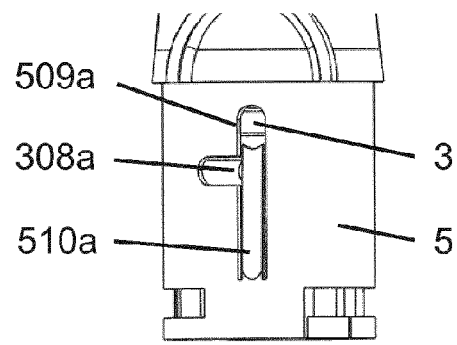
FIG. 51 shows a perspective view of the relative position of the case and the reservoir after the device is unlocked.
Figure 54:
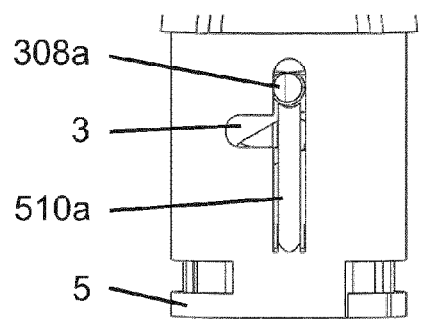
FIG. 54 shows a perspective view of the relative position of the case and the reservoir after the device is safety locked.

When the pens 203a, 203b reach the end of the grooves 305a, 305b, as shown in FIG. 50, further rotation of the foot 1 will cause that the needle hub 2 to start pushing the reservoir 3. The reservoir 3 will then rotate along with the needle hub 2 and the foot 1, causing the pens 308a, 308b to slide through the third grooves 511a, 511b until they are positioned in the second grooves 509a, 509b, as shown in FIG. 51, at which point the rotation of the foot 1 is complete. The snaps 510a, 510b exert an inwardly directed force onto the pens 308a, 308b of the reservoir 3 to ensure that the internal parts reservoir 3, seal 4, needle hub 2 and needle 7 stay in this position and cannot fall downwards due to gravity or due to inertial forces caused by movement of the device 9. Without such friction, movement of the reservoir 3 with respect to the case 5 in a "downward direction" would move the first end 71 of the needle 7 out of the opening 102 prematurely, while movement of the reservoir 3 in an "upward direction" would move the pens 308 into their safety-lock position (FIG. 54). Both movements are prevented by a sufficient friction/resistance between the snaps 510 and the pens 308.

Figure 52:
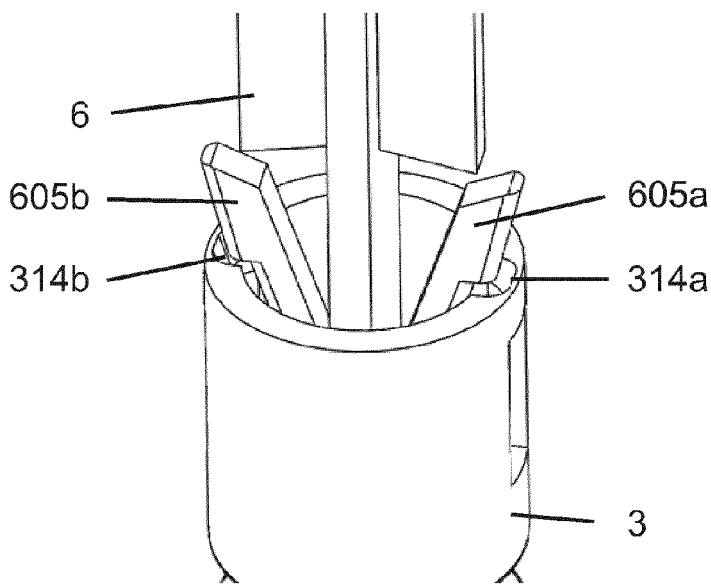
FIG. 52 shows a perspective view of the relative position of the plunger and the reservoir after the device is unlocked.

When the reservoir 3 is rotated along with the foot 1 in respect of the case 5, and thus also with respect to the plunger 6 which cannot rotate in the case 5, the grooves 314a, 314b of the reservoir 3 get aligned underneath the snap heads 605a, 605b of the plunger 6, as shown in FIG. 52. Thus, after the foot 1 is rotated over the predefined angle with respect to the case 5 (in the example above a total angle of 50°+25°=75°, the device 9 is unlocked, the second needle end 72 has penetrated the cavity 315, and the internal parts: reservoir 3, seal 4, needle hub 2, plunger 6 and needle 7 are no longer prevented from moving up or down with respect to the case 5. They are only held in place by the clamping force of the snaps 510.

Besides the locking mechanisms described above, which may be somewhat fragile, there is also a back-up mechanism, as will be described next. During the rotation of the foot 1, the pens 103a, 103b of the foot 1 (see FIG. 3) slide along the first grooves 502a, 502b of the case 5. When the rotation is started, the pens 103a, 103b need to overcome the level difference between the different radial levels 503a, 503b (FIG. 30). This ensures the foot 1 cannot rotate unless a sufficiently large torque is applied, thus avoiding accidental unlocking, e.g. through vibrations during transport. After rotating the foot 1 over the predefined angle (e.g. 50° in the example given above), the pens 103a, 103b are positioned beyond the rib 505 of the case (see FIG. 31). This rib 505 prevents the pens 103a, 103b and thus the foot 1, the needle hub 2, the needle 7 and the reservoir 3 along with it from rotating back to their starting position.

The position of the parts 1-8 of the device 9 after unlocking the device 9, is shown in FIG. 42. The main differences with respect to FIG. 41 are that the second needle end 72 has penetrated the wall section 316, and that the protrusions 109 (FIG. 1) and 517 (FIG. 25) are aligned for indicating to the user that the activation is complete, and that the pens 308 are moved into the longitudinal grooves 509 for allowing movement of the reservoir in the case, and that the snap heads 605 are aligned above the grooves 314 for allowing the plunger 6 to move towards the reservoir 3.

Figure 60:
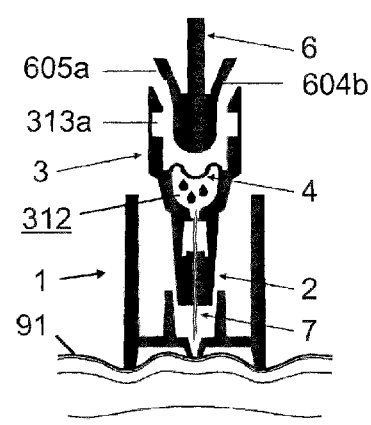
FIG. 60 is a schematic representation of the relative positions of the foot, needle, reservoir, seal and plunger after the device is activated.

This is also schematically illustrated in FIG. 60, showing an example of the relative positions of the foot 1, needle 7, reservoir 3, seal 4, and plunger 6 after the device 9 is activated. As shown, the first end 71 of the needle (bottom end) is still within the device 9, but the second needle end 72 has penetrated into the cavity 315, at the bottom of the actual reservoir 312, which is filled with liquid, e.g. vaccine.

Second Step: Pushing the Plunger, Insertion of the Needle and Actual Injection

The second step comprises the action of the injection in itself, i.e. the delivery of fluid, e.g. drug from the device 9 to the subject. After the device 9 is unlocked (as described above), the collar 101 of the bottom end 121 of the foot 1 is placed on the subject's skin, and the plunger 6 is pressed. This causes the needle 7 to puncture the skin, and to push the liquid out of the reservoir 3 through the needle 7 into the dermis. This action is normally done in a single smooth movement by pressing the plunger 6, but is described next in several small steps.

Figure 25:
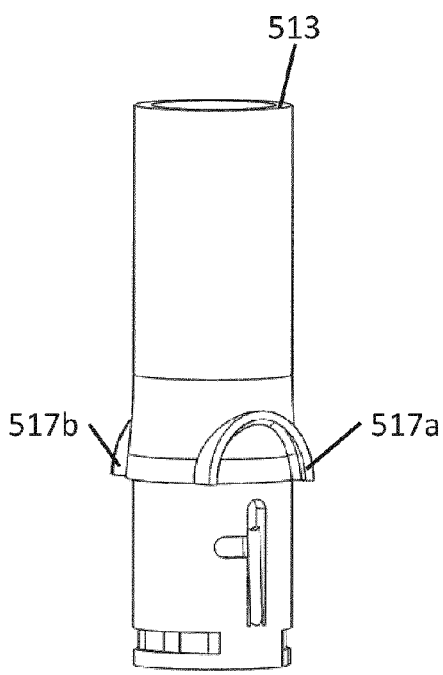
FIG. 25 shows a perspective view of the case of FIG. 20 from above.

After unlocking the device 9, and placing the device 9 on the subject's skin 91, the user pushes the plunger 6, for example with the index finger positioned on the concave surface 607 of the plunger 6 and the thumb and middle finger positioned on the (aligned) protrusions 517a, 517b and 109 (FIG. 1 and FIG. 25). FIG. 59 shows the penetration depth of the needle 7 in the skin 91. The spring 8 provides a predetermined amount of counter pressure which needs to be overcome by the user for initially moving the plunger 6 until the snap heads 605 come into contact with the grooves 314 (FIG. 55 and FIG. 61). When pushing further, in addition to the spring force, also a friction/resistance for inserting the first needle end 71 into the skin, and the friction/resistance between the snaps 510 and the pens 308 need to be overcome, so that the plunger snap heads 605a, 605b will first push the reservoir 3 downwards with respect to the case 5 (i.e. towards the skin), thereby inserting the needle end 71 into the skin 91 (FIG. 62). During this movement the pens 308a, 308b of the reservoir 3 slide along the second grooves 509a, 509b of the case 5 (FIG. 51), hampered by the snaps 510a, 510b.

The resistance between the plunger snap heads 605a, 605b and the grooves 314a, 314b (FIG. 52) of the reservoir 3 must be larger than the resistance generated by the hampering of the snaps 510a, 510b in contact with the pens 308 so that first the reservoir 3 and the needle hub 2 and the needle 7 are moved, but the plunger 6 maintains its position with respect to the space 312 (FIG. 61 and FIG. 62). This ensures that no pressure is exerted by the plunger head 603 on the fluid in the space 312 until after the needle is inserted into the skin, otherwise the snaps 604a, 604b would slide along the grooves 314a, 314b too early, and the intradermal injection would fail because of premature emptying of the reservoir 3. In this way spilling of fluid is avoided. In its downward movement, the plunger 6 initially takes the reservoir 3, the seal 4, the needle hub 2 and the needle 7 along with it. The needle 7 passes through the opening 102, punctures the skin, and the first needle end 71 opening 703 reaches a depth of about 1.0 mm in the dermis (see example FIG. 59). At this moment the parts 1-8 of the device 9 are positioned into the third position, as shown in FIG. 43 and FIG. 62. The contact between the surface 303 of the reservoir 3 (FIG. 11) and the surface 104 of the foot 1 (FIG. 3) limits the penetration depth of the needle 7 into the skin. Alternatively or in combination thereto, the penetration depth L (FIG. 59) may also be limited by the contact between other parts, e.g. the needle hub 2 and the foot 1. The penetration depth L also depends on the positioning of the needle 7 in the needle hub 2.

Figure 63:
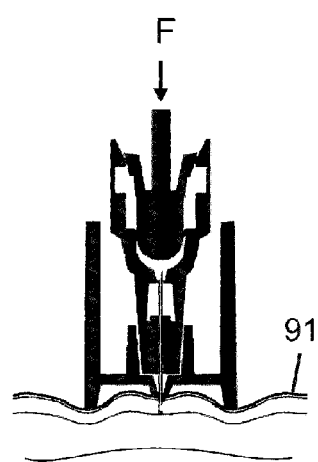
FIG. 63 shows the schematic representation of FIG. 62 when a force is applied to the plunger, and the plunger has moved slightly with respect to the reservoir for squeezing the fluid out of the "actual reservoir" holding the fluid.
Figure 64:
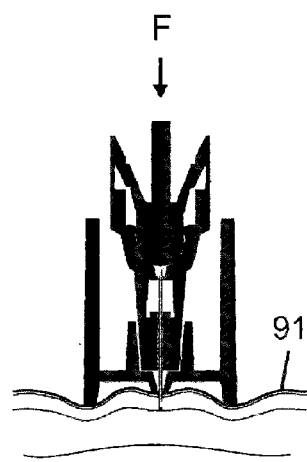
FIG. 64 shows the schematic representation of FIG. 63, when the plunger has moved down to its distal position, and substantially all of the liquid has been squeezed out of the device, and the frictional force between the plunger and reservoir is surmounted.

When the bottom surface 303 of the reservoir 3 contacts the surface 104 of the foot 1 (FIG. 62), the reservoir 3, the needle hub 2, the seal 4 and the needle 7 cannot move further downward with regard to the foot 1 and case 5. If the force exerted upon the plunger top surface 607 is larger than the force to overcome further compression of the spring 8, and to overcome the friction/resistance to move the snap heads 605 into the grooves 314, e.g. by bending the snaps 604 inwards (FIG. 52 and FIG. 53), the plunger 6 can move further down with respect to the case 5, while the reservoir 3 and the needle hub 2 and the needle 7 maintain their position. The head 603 of the plunger 6 is then pushed against the flexible seal 4, located inside the reservoir 3 on top of the space 312 containing the liquid. Movement of the head 603 pushes the liquid out of the space 312, through the needle 7, into the skin (FIG. 63). At the same time the snap heads 605a, 605b of the snaps 604a, 604b slide past the grooves 314a, 314b into the openings 313a, 313b (FIG. 53 and FIG. 64), ensuring the plunger 6 is now directly connected, e.g. hooked, to the reservoir 3 and indirectly also to the other internal parts such as e.g. the needle 7. At this moment the parts of the device 9 are positioned into position 4, as shown in FIG. 44. The spring 8 is now in its most compressed state and stores the energy needed for the next step.

Third Step: Releasing the Plunger, Safety Locking

Figure 53:
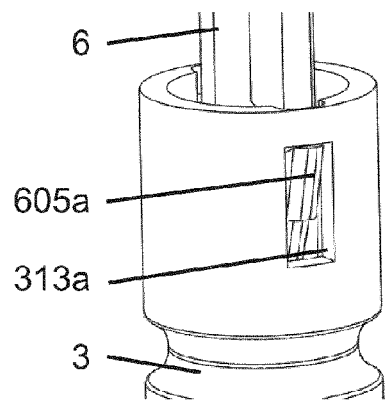
FIG. 53 shows a perspective view of the relative position of the plunger and the reservoir after the liquid is removed from the device.

The third step comprises the safety locking of the device 9. This step is done automatically and the user has no part in it. This step takes place as soon as pressure on the plunger surface 607 is released, which should occur normally after the liquid, e.g. drug, is completely injected. The energy for the safety locking is provided by the compressed spring 8. When the user releases the plunger 6, the spring 8 pushes the plunger 6 upwards. The plunger snap heads 605a, 605b are now positioned in the openings 313a, 313b of the reservoir 3, as shown in FIG. 53, and drag the internal parts (the reservoir 3, the needle hub 2, the needle 7 and the seal 4) along with the plunger 6, away from the foot 1. During this movement the pens 308a, 308b slide again through the second grooves 509a, 509b but now in opposite direction, still hampered by the snaps 510a, 510b. The force of the spring 8 needs to be larger than the resistance exerted by the snaps 510a, 510b upon the pens 308. Finally the pens 308a, 308b of the reservoir 3 are pulled over the snaps 510a, 510b by the spring, as shown in FIG. 54, into the free space/openings at the top of the second grooves 509a, 509b, above the snaps 510a, 510b, which secure the position of the pens 308. This ensures the pens 308a, 308b cannot be pushed downwards again, even if a relatively large force would be exerted upon the plunger 6. Since the internal parts 1-8 cannot be pushed downwards again, the plunger 6 is also locked and there is no way to get to the needle 7 without disassembling the device 9, thus accidental contact with the needle 7 is prevented, and thus contamination and needle stick injuries are avoided. FIG. 45 shows the position of the parts 1-8 of the device 9 in the safety-lock mode.

REFERENCES 1 foot
101 collar
102 opening
103 pen
104 face
105 bevel (of the pen)
106 bevel (of the pen)
107 shaft
108 extra walls
109 holding shape
110 indications
111 longitudinal axis
112 second collar (around opening)
121 bottom end
122 top end
2 needle hub
201 main body
202 bulge
203 pen
204 bevel
205 bevel
206 opening
207 bottom
3 reservoir
301 first hollow segment
302 second hollow segment
303 distal surface
304 surface
305 groove
306 wall
307 groove
308 pen
309 rounded end
310 bevel
311 dividing wall
312 hollow space
313 opening
314 groove
315 cavity
316 wall section
4 seal
401 surface
402 end portion
5 case
501 segment
502 first groove
503a upper level
503b lower level
504 bevel
505 rib
506 insertion portion
507 delimiting wall
508 surface
509 second groove
510 snap
511 third groove
512 fourth groove
513 upper surface
514 circular opening
515 second opening
516 first end of case
517 second end of case 518 top end
519 open end
6 plunger
601 main body
602 secondary body
603 plunger head
604 snap
605 snap head
606 rib
607 top surface
608 surface
7 needle
71 first end
72 second end
701 first bevel
702 second bevel
703 first opening
704 second opening
8 spring
9 device
91 skin

ADVANTAGES OF THE CURRENT INVENTION

Embodiments of the present invention may show one or more, optionally all, of the following advantages:

1. Safety: proper activation-deactivation mechanism may be in place in order to avoid needle stick accidents and re-use of the device 9. Also the needle may be hidden in the device 9.
2. Activation step: solution, e.g. drug, can only be released after activation of the device 9.
3. Inactivation step: the needle may be retracted into the device 9 after injection of the fluid, e.g. drug in the reservoir. The reservoir may be emptied completely before the inactivation step may be initiated. The needle cannot be reached afterwards.
4. Recycling: all components can be constructed in polymer materials which is advantageous for recycling purposes.
5. Type of needle: a needle having a diameter in the range of 26 G to 34 G, with a length of e.g. about 5.0 mm corresponding to a penetration depth L (FIG. 59) of less than 1.5 mm, e.g. equal to about 1.0 mm is envisioned, as can be used for children, elderly and adults and allows injection at anatomic sites other than the deltoid where the skin surface is less thick, e.g. forearm.
6. Stability: perpendicular positioning of the skin onto the needle 7, may be ensured by the collar 101 and may provide additional stability and may allow the use of thin needles.
7. Logistics: as a smaller amount of fluid is required in the present device 9, a small total volume and therefore less storage, cooling and transport space may be needed.
8. Reservoir: together with the described mechanism to empty the space 312 it may have one or more of the following advantages: minimum overfill, completely sealed system, integrated part of the device 9, i.e. cannot be refilled after use, alignment plunger and emptying of the reservoir. Different filling procedures can be used to fill the reservoir with liquid, e.g. drug.
9. Self-administration: opportunity for self-administration at an easily accessible anatomic site compared to self-administration at the deltoid location only.

The invention claimed is:

1. An intradermal injection device, comprising:
a housing;
a foot mounted to the housing, and having a surface which can be placed on a subject's skin to be injected, and having an opening for allowing passage of a needle;
a reservoir movably mounted in the housing, and having a hollow space for holding a fluid to be administered to the subject, wherein the reservoir has a dividing wall forming a bottom of the hollow space for holding the fluid;
a hollow needle movably mounted in the housing such that it can selectively protrude through the opening or be retracted from the opening, and having a first end for penetrating the subject's skin and a second end for penetrating the reservoir, the first end having a first opening for administering the fluid to the subject, the second end having a second opening for accepting the fluid from the reservoir and passing it through the needle to the first end;
a plunger movably mounted in the housing for moving the needle through the opening for penetrating the subject's skin, and for pressing the fluid out of the reservoir into the needle;
wherein
the reservoir is frictionally mounted inside the housing by a first frictional mounting, and the plunger is frictionally mounted to the reservoir by a second frictional mounting in such a way that the force required to overcome the resistance to move the plunger with respect to the reservoir is at least a predetermined amount larger than the force required to overcome the friction to move the reservoir with respect to the housing, and wherein the plunger has a plunger head with a shape complimentary to the shape of the dividing wall of the reservoir.

2. The intradermal injection device according to claim 1, wherein the reservoir comprises a cavity for receiving the second end of the needle, the cavity being in fluid connection with the hollow space and having a volume less than 3% of the volume of the hollow space.

3. The intradermal injection device according to claim 1, further comprising an elastic seal for closing the hollow space, and for squeezing substantially all of the fluid out of the hollow space when the plunger is moved towards the needle.

4. The intradermal injection device according to claim 1, wherein the needle is fixedly mounted in a needle hub, the needle hub being movably mounted between the foot and the reservoir, and wherein the needle has an inner diameter in the range of 0.0826 mm to 0.260 mm.

5. The intradermal injection device according to claim 4, wherein the needle hub is movably mounted between the foot and the reservoir by means of a wall extending from the foot, the wall and the needle hub being adapted to engage, so as to allow axial movement with respect to the foot.

6. The intradermal injection device according to claim 1, wherein the needle is fixedly mounted in a needle hub, and wherein the needle hub has at least one protruding pen adapted for being received in at least one groove of the reservoir,
and wherein the housing comprises a tubular case having a first end for receiving the plunger and a second end for receiving the reservoir and the needle hub and the foot,
the foot having means for angularly engaging the needle hub, the case having a groove ending in an opening for receiving a pen protruding from the reservoir for movably mounting the reservoir to the case, the case further having another groove for receiving at least one pen penetrating inwardly from the foot for movably mounting the foot to the case.

7. The intradermal injection device according to claim 6, wherein the case has at least one opening for receiving at least one rib of a plunger for preventing rotation of the plunger, and wherein the plunger has snaps not being aligned above grooves of the reservoir in a locked mode, and the reservoir has protruding pens received in a circumferential groove of the case, so that the plunger and the reservoir are prevented from axial movement in the locked mode.

8. The intradermal injection device according to claim 6, wherein the groove of the reservoir is inclined with respect to a plane perpendicular to the longitudinal axis of the device and whereby the case further comprises longitudinal grooves in connection with the opening, so that a rotation of the foot results in an axial displacement of the needle hub towards the reservoir, and in that the protruding pens are moved into the longitudinal grooves, and in that the snaps of the plunger are aligned above the grooves of the reservoir in an unlocked mode.

9. The intradermal injection device according to claim 6, wherein the groove of the case has at least one rib forming a hook for obstructing the pen of the foot for preserving the angular position of the foot with respect to the case.

10. The intradermal injection device according to claim 8, wherein the longitudinal grooves of the case comprise at least one snap for exerting a pressure directed inwardly upon the protruding pens of the reservoir for creating the frictional mounting between the case and the reservoir, and wherein the protruding pens of the reservoir have a bevel for enabling the move of the protruding pens from the opening towards the longitudinal grooves against the pressure of the snaps.

11. The intradermal injection device according to claim 9, wherein the longitudinal grooves of the case comprise at least one snap for exerting a pressure directed inwardly upon the protruding pens of the reservoir for creating the frictional mounting between the case and the reservoir, and wherein the protruding pens of the reservoir have a bevel for enabling the move of the protruding pens from the opening towards the longitudinal grooves against the pressure of the snaps.

12. The intradermal injection device according to claim 1, furthermore comprising a safety lock, the safety lock comprising a spring for withdrawing the needle back into the opening when pressure on the plunger is released and the device is in unlocked mode, and for blocking the needle after being withdrawn.

13. The intradermal injection device according to claim 6,
wherein the plunger has at least one snap, and the groove of the reservoir has at least one opening for receiving the snap when the plunger has reached its distal position for permanently fixing the position of the plunger with respect to the reservoir;

and wherein the groove of the case further has an open end for receiving the pen of the reservoir when the reservoir is completely withdrawn, and wherein the snap of the case further has a top end for permanently fixing the position of the reservoir with respect to the case.

* * * * *